United States Patent
Teratani et al.

(10) Patent No.: US 10,561,122 B2
(45) Date of Patent: Feb. 18, 2020

(54) GENETICALLY MODIFIED RAT DERIVED FROM RAT EMBRYONIC STEM CELL

(71) Applicants: SUMITOMO CHEMICAL COMPANY, LIMITED, Tokyo (JP); National Cancer Center, Tokyo (JP)

(72) Inventors: Takumi Teratani, Yokohama (JP); Takahiro Ochiya, Tokyo (JP)

(73) Assignees: SUMITOMO CHEMICAL COMPANY, LIMITED, Tokyo (JP); National Cancer Center, Tokyo (JP)

( * ) Notice: Subject to any disclaimer, the term of this patent is extended or adjusted under 35 U.S.C. 154(b) by 388 days.

(21) Appl. No.: 15/645,636

(22) Filed: Jul. 10, 2017

(65) Prior Publication Data

US 2017/0311578 A1 Nov. 2, 2017

Related U.S. Application Data

(62) Division of application No. 14/132,969, filed on Dec. 18, 2013, now Pat. No. 9,700,023, which is a division of application No. 13/370,795, filed on Feb. 10, 2012, now Pat. No. 8,628,957, which is a division of application No. 10/591,407, filed as application No. PCT/JP2005/003841 on Mar. 1, 2005, now Pat. No. 8,137,966.

(30) Foreign Application Priority Data

Mar. 4, 2004 (JP) ................................. 2004-061300
Oct. 26, 2004 (JP) ................................. 2004-310465

(51) Int. Cl.
| | | |
|---|---|---|
| A01K 67/027 | (2006.01) | |
| C12N 15/00 | (2006.01) | |
| C12N 15/82 | (2006.01) | |
| C12N 5/0735 | (2010.01) | |
| C12N 15/873 | (2010.01) | |
| G01N 33/50 | (2006.01) | |

(52) U.S. Cl.
CPC ........ A01K 67/0275 (2013.01); C12N 5/0606 (2013.01); C12N 15/873 (2013.01); G01N 33/5073 (2013.01); A01K 2217/05 (2013.01); A01K 2227/105 (2013.01); A01K 2267/0393 (2013.01); C12N 2501/235 (2013.01)

(58) Field of Classification Search
CPC ............ A01K 67/0275; A01K 67/0276; A01K 67/0278; A01K 2227/105; C12N 5/0606; C12N 15/873
See application file for complete search history.

(56) References Cited

U.S. PATENT DOCUMENTS

| | | |
|---|---|---|
| 5,631,153 A | 5/1997 | Capecchi |
| 7,105,717 B1 | 9/2006 | Shirai et al. |
| 7,297,539 B2 | 11/2007 | Mandalam et al. |
| 9,700,023 B2 * | 7/2017 | Teratani ............. A01K 67/0275 |
| 2002/0188963 A1 | 12/2002 | Loring |
| 2005/0164377 A1 | 7/2005 | Miyabayashi et al. |

FOREIGN PATENT DOCUMENTS

| | | |
|---|---|---|
| JP | 05-304951 A | 11/1993 |
| JP | 2002-176973 A | 6/2002 |
| WO | WO 1995/006716 A1 | 3/1995 |
| WO | WO 1998/030679 A1 | 7/1998 |
| WO | WO 1999/027076 A1 | 6/1999 |
| WO | WO 2003/038070 A1 | 5/2003 |

OTHER PUBLICATIONS

Brenin et al., *Developmental Biology*, 185: 124-125 (1997).
Buehr et al., *Biology of Reproduction*, 68: 222-229 (2003).
Buehr et al., *Cell*, 135: 1287-1298 (2008).
Demers et al., *Cloning and Stem Cells*, 9(4): 512-522 (2007).
Evans et al., *Nature*, 292: 154-156 (Jul. 1981).
Hirabayashi et al., "Rat Embryonic Stem Cells: Establishment and Their Use for Transgenesis," in *Methodological Advances in the Culture, Manipulation and Utilization of Embryonic Stem Cells for Basic and Practical Applications*, Atwood, C. (ed.) [published by InTech], Chapter 22, pp. 397-410 (Apr. 26, 2011).
Iannaccone et al., *Developmental Biology*, 163: 288-292 (1994).
Iannaccone et al., *Developmental Biology*, 185: 124-125 (1997).
Kawamata and Ochiya, "Establishment of Embryonic Stem Cells and Generation of Genetically Modified Rats," *Methodological Advances in the Culture, Manipulation and Utilization of Embryonic Stem Cells for Basic and Practical Applications*, Atwood, C. (ed.) [published by InTech], Chapter 21, pp. 383-396 (Apr. 26, 2011).
Li et al., "Germline Competent Embryonic Stem Cells Derived from Rat Blastocysts," *Cell*, 135(7): 1299-1310 (2008).
Li et al., *Cell Research*, 19: 173-186 (2009).
Loring, *Methods in Molecular Medicine*, 32: 249-270 (1999).
Suemori et al., *Methods in Enzymology*, 365: 419-429 (2003).
Takahama et al., *Oncogene*, 16: 3189-3196 (1998).

(Continued)

*Primary Examiner* — Quang Nguyen
(74) *Attorney, Agent, or Firm* — Leydig, Voit & Mayer, Ltd.

(57) ABSTRACT

The present invention provides a rat embryonic stem cell characterized by having the following properties of (a) expressing Oct3/4 gene and Nanog gene, (b) positive for alkaline phosphatase activity, (c) having an embryoid body forming ability, (d) expressing SSEA (Stage-Specific Embryonic Antigen)-1 and SSEA-4, (e) having the same number of chromosomes as does a normal rat cell, (f) capable of being subcultured and holding the undifferentiated state, (g) having in vitro pluripotency, (h) having a potential to differentiate for cells of three embryonic germ lineages, (i) having teratoma formation ability, and (j) having an ability to produce a chimeric rat, a method of establishing the aforementioned rat embryonic stem cell and the like.

2 Claims, 14 Drawing Sheets

Specification includes a Sequence Listing.

(56) References Cited

OTHER PUBLICATIONS

Takahama et al., *The Molecular Biology Society of Japan Nenkai Program Koen Yoshishu*, 20: 562, Abstract No. 3-510-P-589 (1997).
Thomson et al., *Current Topics in Developmental Biology*, 38: 133-165 (1998).
Thomson et al., *Proc. Natl. Acad. Sci. USA*, 92: 7844-7848 (Aug. 1995).
Ueda et al., *PLoS One*, 3(7): e2800 [pp. 1-9] (2008).
Vassilieva et al., *Experimental Cell Research*, 258: 361-373 (2000).
Yamanaka et al., *Anim. Sci. J.*, 72: 285-290 (2001).
Zhou et al., *Science*, 302: 1179 (2003).

* cited by examiner

Establishment method of rat ES cells a) x 100   b) x 200   c) x 400

```
                        SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
agagcaagag aggtatcctg                                              20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
agagcatagc cctcgtagat                                              20

<210> SEQ ID NO 3
<211> LENGTH: 21
<212> TYPE: DNA
<213> ORGANISM: Artificial Sequence
<220> FEATURE:
<223> OTHER INFORMATION: PCR Primer
```

```
<400> SEQUENCE: 3
atggactacc cagaacccca g                                              21

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
ttacaggagc tgcagttata c                                              21

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
tagccctgat tcttctagca                                                20

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
tttgctgcaa cggcacataa                                                20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
aaatcatgac gaggcaaggc                                                20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tgagttcgct ccaacagtct                                                20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
acctgagccc cggcacacag                                                20

<210> SEQ ID NO 10
```

```
<211> LENGTH: 20
<212> TYPE: DNA
<213> ORGANISM: Artificial Sequence
<220> FEATURE:
<223> OTHER INFORMATION: PCR primer

<400> SEQUENCE: 10
cagctgcagc ggtgtgggcg                                              20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
gctctgacct atcatctgag                                              20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
agatgcacag gagatgctac                                              20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
ggaacgcatc agtgtctact                                              20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
accacgctga aggtgttcat                                              20

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
tctcactgct tatggtccga                                              20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
```
tcagtggtac ccattggtga                                                  20

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
ggctctgaga gagattcgca                                                  20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
atgtccaggg ctagcttaac                                                  20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
tctgaagcgg cagaagaatc                                                  20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
tgacctcgat gaacttggga                                                  20

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
atacagtgcg gtgtccaaca                                                  20

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
ttatcttcgg taccggaagc                                                  20

<210> SEQ ID NO 23
<211> LENGTH: 20
<212> TYPE: DNA

```
<213> ORGANISM: Artificial Sequence
<220> FEATURE:
<223> OTHER INFORMATION: PCR primer

<400> SEQUENCE: 23
tgcggatgct gcatgttgat                                              20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
caaacccaga gccaagtatg                                              20

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
gcttgctgtg ataagccagt                                              20

<210> SEQ ID NO 26
<211> LENGTH: 20
<212> TYPE: DNA
<213> ORGANISM: Artificial Sequence
<220> FEATURE:
<223> OTHER INFORMATION: PCR primer

<400> SEQUENCE: 26
tggcagacag atagtcttcc                                              20

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
cgatgagaag cgtcatgact                                              20

<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
aaccaggtac gatgagaggt                                              20

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
aatgagattc gagacgggct                                              20
```

```
<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ttcatcacag tggtagtgct                                              20

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
gtcaacgtat ggattccggt                                              20

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
gttctccttt gcagctcttg                                              20
```

GENETICALLY MODIFIED RAT DERIVED FROM RAT EMBRYONIC STEM CELL

CROSS-REFERENCE TO RELATED APPLICATIONS

This patent application is a divisional of copending U.S. patent application Ser. No. 14/132,969, filed on Dec. 18, 2013, which is a divisional of U.S. patent application Ser. No. 13/370,795, filed on Feb. 10, 2012, now issued as U.S. Pat. No. 8,628,957, which is a divisional of U.S. patent application Ser. No. 10/591,407, filed on Dec. 8, 2006, now issued as U.S. Pat. No. 8,137,966, which is the U.S. national phase of International Patent Application No. PCT/JP2005/003841, filed on Mar. 1, 2005, which claims the benefit of Japanese Patent Application No. 2004-310465, filed on Oct. 26, 2004, and Japanese Patent Application No. 2004-061300, filed on Mar. 4, 2004, all of which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,261 bytes ASCII (Text) file named "728976SequenceListing.txt," created Jul. 7, 2017.

TECHNICAL FIELD

The present invention relates to rat embryonic stem cells (hereinafter to be referred to as ES cells). More particularly, the present invention relates to rat ES cells, production methods of rat ES cells, subculture methods of rat ES cells, screening methods for a differentiation induction-related substance using rat ES cells, use of the aforementioned rat ES cells for the production of a genetically modified rat and the like.

BACKGROUND ART

ES cells are cells of cell lines established from an inner cell mass of blastocysts, and autonomously replicable in the presence of a leukemia inhibitory factor (LIF). ES cells can be differentiated into any type of cells (neuron, myocyte, vascular endothelial cell, erythrocyte, leukocyte, platelet, bone, cartilage, kidney, intestine, liver, pancreas, lung and the like) by changing culture conditions. Genomes of many kinds of animals have been decoded as the results of genome projects, and the information of their homologies with humans has been accumulated. The destruction of a particular gene in the stage of ES cells based on these information may elucidate a role (function) of the gene in cell differentiation, or growth of individual, homeostasis or the like. Specifically, a chimeric animal can be produced by injecting ES cells, in which a particular gene has been destructed, into normal host blastocysts to be mixed with the cells of the host embryos and returning the mixture to a uterus, and an animal, in which the particular gene has been destructed (knockout animal), can be produced by crossing the obtained chimeric animals. In addition, the effects of a compound on genes in various cells (organs) can be evaluated by applying the compound to ES cells. On the other hand, a use of normal cells obtained by differentiating ES cells enables cell therapy and regenerative medicine. As mentioned above, ES cells can be widely applied to studies in physiology, pharmacology, regenerative medicine and the like. However, in experimental animals, ES cells derived from only mouse (Evans M. J. et al., *Nature* 1981, 292: 154-156), rhesus monkey (Thomson J. A. et al., *Proc. Natl. Acad. Sci. USA* 1995, 92: 7844-7848), marmoset (Thomson J. A., et al., *Cur. Top. Dev. Biol.* 1998, 38: 133-165) and crab-eating monkey (Suemori H, et al., *Methods Enzymol.* 2003, 365: 419-429) have been established, and a rat ES cell has not been established yet.

Rat is a mammal having a size suitable for experiments (about 10 times the size of mouse), and it is advantageous in that (1) a drug can be easily administered to a minute blood vessel, (2) surgical and transplant experiments can be performed and (3) a large amount of tissue can be obtained. Many human disease model rats have been developed and discovered. Rat is one of the most useful experimental animals, which is widely utilized in various fields including medicine. For the past 100 years, rat has been utilized for the studies in functions and the like as a model for cancer, cerebral nerve system, transplantation and human multifactorial disorder, and a vast amount of functional research resources has been accumulated. Particularly, the analysis of brain atlas is ongoing and abundant information of behavioral study in psychophysiology is available. As regards gene analysis, which is the weakest point as compared to mouse, too, since the analysis of rat genome is advancing, comparison with human at the gene level has been enabled, and rat has been drawing attention as an excellent experimental animal leading the post-genome. In fact, the Bioresource Area Subcommitte, the Life Science Subcommittee, the Subdivision on R&D planning and Evaluation, the Council for Science and Technology held in March, 2002 admitted that rat was one of the bioresources that should be enriched in Japan in the future, and that establishment of ES cells for the purpose of production of knockout rats was necessary.

Despite such utilities of rat and enrichment of genetic information therearound and the like, it has been extremely difficult to establish rat ES cells essential for the production of a genetically modified rat. For example, Iannaccone, P. M. et al. (*Developmental Biology* 1994, 163: 288-292) and the corresponding patent application WO 95/06716 describe that ES cells have been established from the rat strain PVG and chimeric rats have been produced. Thereafter, however, Brenin, D. et al. (*Developmental Biology* 1997, 185: 124-125) describe that the chimeric rats produced in *Developmental Biology* 1994, 163: 288-292 were produced by the contamination of mouse ES cells. Namely, it has been shown that they did not succeed in the establishment of rat ES cells and the production of chimeric rat. There are some other cases where the establishment of rat ES cell was attempted (see WO 99/27076 and JP 2002-176973 A), but all of them have not succeeded in the establishment.

As mentioned above, plural research groups have unsuccessfully tried to establish rat ES cell lines. In the INTERNATIONAL CONGRESS ON STEM CELLS held in Keystone in April 2004 in the United States, it was recognized that there had been no report on the establishment of rat ES cells all over the world. A key to the successful establishment of rat ES cells is the setting of culture conditions for the production of ES cells. While the conventional attempts have been made based on the establishment of and culture conditions for mouse ES cells, rat ES cells have not been established as yet. From these backgrounds, it is considered that ingenuity in the culture conditions is essential for the production of rat ES cells.

DISCLOSURE OF THE INVENTION

It is an object of the present invention to provide rat ES cells not available heretofore. It is also an object of the present invention to provide a method of establishing and producing rat ES cells, a method of subculturing rat ES cells, a method of screening for a differentiation induction-related substance using rat ES cells, and a use of the aforementioned rat ES cells for the production of a genetically modified rat and the like.

The present inventors tried to establish rat ES cells from blastocysts derived from various rat strains and determined culture conditions and passage conditions, which are completely different from those for mouse ES cells, thereby successfully establishing rat ES cell lines. Specifically, the present inventors first succeeded in establishing and supplying rat ES cells, which are stable and meet all of the requirements of ES cells, by the use of a culture medium substantially free of serum, and by trying various measures such as attempting establishment by mechanical means for isolation of inner cell mass and passage of ES cells.

The present invention has been completed based on these findings.

Accordingly, the present invention is listed in the following:

(1) a rat embryonic stem cell characterized by having the following properties (a)-(j):
(a) expressing Oct3/4 gene and Nanog gene,
(b) positive for alkaline phosphatase activity,
(c) having an embryoid body forming ability,
(d) expressing SSEA (Stage-Specific Embryonic Antigen)-1 and SSEA-4,
(e) having the same number of chromosomes as does a normal rat cell,
(f) capable of being subcultured and holding the undifferentiated state,
(g) having in vitro pluripotency,
(h) having a potential to differentiate for cells of three embryonic germ lineages,
(i) having teratoma formation ability,
(j) having an ability to produce a chimeric rat,
(2) the rat embryonic stem cell of the aforementioned (1), further having the property:
(k) differentiating by culture in the presence of 20% serum,
(3) a rat embryonic stem cell obtained by performing a process comprising the following steps (A)-(D), under the culture conditions using a substantially serum free culture medium:
(A) a step for dissociating an inner cell mass formed by the culture of rat blastocysts, remaining a state of cell aggregate,
(B) a step for culturing primary embryonic stem cells resulting from the culture of the dissociated inner cell mass until it can be passaged,
(C) a step for dissociating the primary embryonic stem cells, which have become capable of being passaged, remaining a state of cell aggregate, followed by passaging and culturing the same,
(D) a step for further passaging and culturing the cells to establish an embryonic stem cell,
(4) the embryonic stem cell of the aforementioned (3), wherein the culture medium comprises a serum replacement reagent,
(5) the embryonic stem cell of the aforementioned (3) or (4), wherein the step (A) comprises a step for mechanically dissociating the inner cell mass,
(6) the embryonic stem cell of any of the aforementioned (3)-(5), wherein the step (C) comprises a step for mechanically dissociating the embryonic stem cells,
(7) the embryonic stem cell of any of the aforementioned (3)-(6), wherein a culture medium without rat leukemia inhibitory factor (rLIF) is used in step (A),
(8) the embryonic stem cell of any of the aforementioned (3)-(7), wherein an rLIF-containing culture medium is used in steps (B)-(D),
(9) the embryonic stem cell of any of the aforementioned (3)-(8), wherein feeder cells are used in the culture,
(10) the embryonic stem cell of the aforementioned (9), wherein the feeder cells are embryo-derived normal fibroblasts,
(11) the embryonic stem cell of any of the aforementioned (1)-(10), which is derived from either strain of Wistar Kyoto strain (WKY), Wistar Hannover GALAS strain (WHG) and Brown Norway strain (BN),
(12) a production method of a non-mouse embryonic stem cell which comprises performing a process comprising the following steps (A)-(D), under the culture conditions using a substantially serum free culture medium:
(A) a step for dissociating an inner cell mass formed by the culture of rat blastocysts, remaining a state of cell aggregate,
(B) a step for culturing primary embryonic stem cells resulting from the culture of the dissociated inner cell mass until it can be passaged,
(C) a step for dissociating the primary embryonic stem cells, which have become capable of being passaged, remaining a state of cell aggregate, followed by passaging and culturing the same,
(D) a step for further passaging and culturing the cells to establish an embryonic stem cell,
(13) the production method of the aforementioned (12), wherein the non-mouse embryonic stem cell is a rat embryonic stem cell,
(14) the production method of the aforementioned (12) or (13), wherein the culture medium comprises a serum replacement reagent,
(15) the production method of any of the aforementioned (12)-(14), wherein the step (A) comprises a step for mechanically dissociating the inner cell mass,
(16) the production method of any of the aforementioned (12)-(15), wherein the step (C) comprises a step for mechanically dissociating the embryonic stem cells,
(17) the production method of any of the aforementioned (12)-(16), wherein an rLIF-free culture medium is used in step (A),
(18) the production method of any of the aforementioned (12)-(17), wherein an rLIF-containing culture medium is used in steps (B)-(D),
(19) the production method of any of the aforementioned (12)-(18), wherein feeder cells are used in the culture,
(20) the production method of the aforementioned (19), wherein the feeder cells are embryo-derived normal fibroblasts,
(21) the production method of any of the aforementioned (13)-(20), wherein the rat embryonic stem cell is derived from either strain of Wistar Kyoto strain (WKY), Wistar Hannover GALAS strain (WHG) and Brown Norway strain (BN),
(22) a subculture method of non-mouse embryonic stem cells which comprises dissociating and passaging the cells, remaining a state of cell aggregate,

(23) the subculture method of the aforementioned (22), wherein the non-mouse embryonic stem cell is a rat embryonic stem cell,

(24) the subculture method of the aforementioned (22) or (23), which comprises a step for mechanically dissociating the cells,

(25) the subculture method of any of the aforementioned (22)-(24), wherein the cells are cultured using a culture medium substantially free of serum,

(26) the subculture method of the aforementioned (25), wherein the culture medium comprises a serum replacement reagent,

(27) the subculture method of the aforementioned (25) or (26), wherein the culture medium comprises rLIF,

(28) a culture medium for non-mouse embryonic stem cell, which comprises a serum replacement reagent and rLIF,

(29) the culture medium of the aforementioned (28), wherein the non-mouse embryonic stem cell is a rat embryonic stem cell,

(30) a culture kit for non-mouse embryonic stem cell, which comprises a serum replacement reagent and rLIF as components,

(31) the culture kit of aforementioned (30), wherein the non-mouse embryonic stem cell is a rat embryonic stem cell,

(32) the culture kit of the aforementioned (31), which further comprises the rat embryonic stem cell of the aforementioned (1)-(11) as a component,

(33) the culture kit of any of the aforementioned (30)-(32), which further comprises feeder cells,

(34) the culture kit of the aforementioned (33), wherein the feeder cells are embryo-derived normal fibroblasts,

(35) a differentiation induction method of a rat embryonic stem cell, which comprises stimulating the rat embryonic stem cell of the aforementioned (1)-(11) with a differentiation inducer,

(36) the differentiation induction method of the aforementioned (35), wherein the differentiation inducer is a retinoic acid, growth factor, glucocorticoid or extracellular substrate,

(37) a cell obtained by inducing the differentiation of the rat embryonic stem cell of any of the aforementioned (1)-(11),

(38) a cDNA library, genomic library or cell extract derived from the rat embryonic stem cell of any of the aforementioned (1)-(11),

(39) a screening method of a differentiation inducer for tissue or cell, which comprises the following steps (i)-(iii):

(i) a step for bringing a test substance into contact with the rat embryonic stem cell of any of the aforementioned (1)-(11), (ii) a step for evaluating the presence or absence or the extent of the differentiation of the rat embryonic stem cell, (iii) a step for judging whether or not the test substance is a substance associated with differentiation induction, based on the evaluation results of the above-mentioned (ii),

(40) a screening method of a substance acting on the differentiation induction of tissue or cell, which comprises the following steps (I)-(III):

(I) a step for bringing a test substance into contact with the rat embryonic stem cell of any of the aforementioned (1)-(11), (II) a step for culturing the rat embryonic stem cell of the aforementioned (I) under the conditions allowing differentiation induction of the embryonic stem cell, and evaluating the presence or absence or the extent of the differentiation thereof, (III) a step for judging whether or not the test substance is a substance acting on the differentiation induction of tissue or cell, based on the evaluation results of the above-mentioned (II),

(41) a use of the rat embryonic stem cell of any of the aforementioned (1)-(11) in the production of a genetically modified rat,

(42) the use of the aforementioned (41), wherein the genetically modified rat is either of a chimeric rat, knockout rat, knockin rat, transgenic rat and knockdown rat,

(43) a production method of a genetically modified rat, which comprises performing a process comprising the following steps (X)-(Z):

(X) a step for introducing a desired gene into the rat embryonic stem cell of any of the aforementioned (1)-(11), (Y) a step for preparing an egg for transplantation comprising the rat embryonic stem cell into which the gene was introduced, (Z) a step for transferring the oocytes for transplantation into a pseudopregnant female rat to produce an offspring rat,

(44) a genetically modified rat produced by the production method of the aforementioned (43),

(45) the rat of the aforementioned (44), which is either of a chimeric rat, knockout rat, knockin rat, transgenic rat and knockdown rat,

(46) a rat embryonic stem cell obtained by performing a process comprising the following steps (A)-(D), under the culture conditions using a culture medium substantially free of serum:

(A) a step for dissociating an inner cell mass formed by the culture of rat blastocysts, remaining a state of cell aggregate, (B) a step for culturing primary embryonic stem cells resulting from the culture of the dissociated inner cell mass until it can be passaged, (C) a step for dissociating the primary embryonic stem cells, which have become capable of being passaged, remaining a state of cell aggregate, followed by passaging and culturing the same, (D) a step for further passaging and culturing the cells to establish a embryonic stem cell, and characterized by having the following properties (a)-(j):

(a) expressing Oct3/4 gene and Nanog gene,
(b) positive for alkaline phosphatase activity,
(c) having an embryoid body forming ability,
(d) expressing SSEA (Stage-Specific Embryonic Antigen)-1 and SSEA-4,
(e) having the same number of chromosomes as does a normal rat cell,
(f) capable of being subcultured and holding the undifferentiated state,
(g) having in vitro pluripotency,
(h) having a potential to differentiate to cells of three embryonic germ lineages,
(i) having teratoma formation ability,
(j) having an ability to produce a chimeric rat,

(47) the rat embryonic stem cell of the aforementioned (46), further having the property:

(k) differentiating by culture in the presence of 20% serum, and

(48) the embryonic stem cell of the aforementioned (46) or (47), which is derived from either strain of Wistar Kyoto strain (WKY), Wistar Hannover GALAS strain (WHG) and Brown Norway strain (BN).

BEST MODE FOR EMBODYING THE INVENTION

Figure 1:
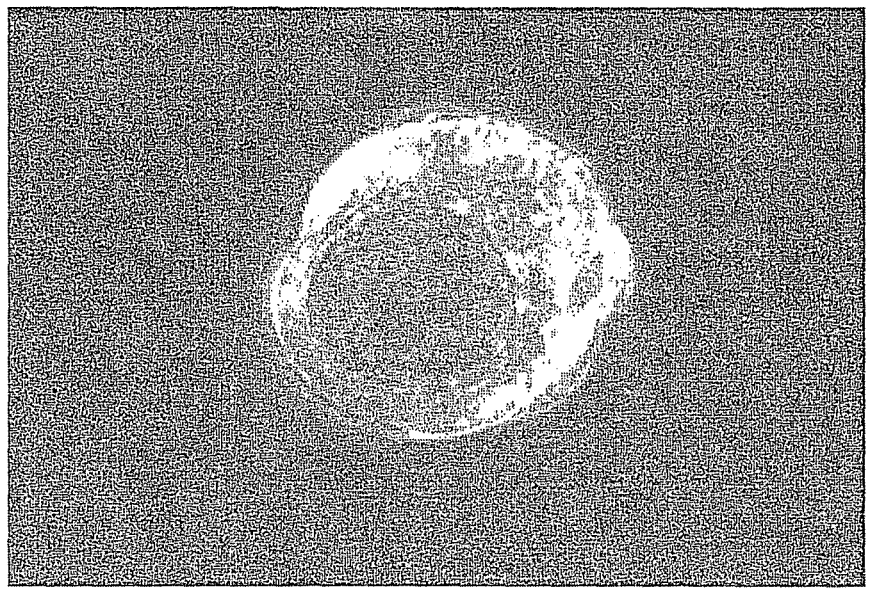
FIG. 1 is a photograph of the rat blastocysts (late stage) used for the establishment of rat ES cells.

The present invention provides rat ES cells that could not be obtained by conventional methods for the first time.

The rat ES cells of present invention can be established and produced by performing a process comprising the following steps (A)-(D), under the conditions using a substantially serum free culture medium:
(A) a step for dissociating an inner cell mass formed by the culture of rat blastocysts, remaining a state of cell aggregate,
(B) a step for culturing primary embryonic stem cells resulting from the culture of the dissociated inner cell mass until it can be passaged,
(C) a step for dissociating the primary embryonic stem cells, which have become capable of being passaged, remaining a state of cell aggregate, followed by passaging and culturing the same, and
(D) a step for further passaging and culturing the cells to establish a embryonic stem cell.

The characteristics of the method for rat ES cell establishment of the present invention is that (1) a substantially serum free culture medium is used in all of the culture of blastocysts, inner cell masses and ES cells, and that (2) in the step for dissociating (exfoliating) inner cell masses and ES cells, the cells are not made to single cells but dissociated (exfoliated) with a certain amount of cell aggregate maintained.

Hereinafter, the method for rat ES cell establishments, the method for characterizing established rat ES cells and the method for subculturing rat ES cells and the like of the present invention are explained.

1. Rat

A rat from which the rat ES cells of the present invention are derived may be any strain of rat, as long as it can establish ES cells based on the aforementioned characteristics of the establishment method of the present invention. For example, it is selected from the rat strains such as Wistar Kyoto strain (WKY), Brown Norway strain (BN), Goto-Kakizaki strain (GK), SD strain, F344/Du strain (Fischer), Wistar strain, Wistar Hannover strain, ACI strain and the like.

2. Feeder Cells

It is preferable to use feeder cells for the establishment and the subsequent culture of rat ES cells of the present invention. Feeder cells may be ones derived from any species available to one of ordinary skill in the art, and are preferably normal fibroblasts rather than established lines of feeder cells. Specifically, normal mouse embryonic fibroblasts can be mentioned. More specifically, primary cultured cells of mouse embryonic fibroblasts (normal fibroblasts) between the 12th and 16th days of pregnancy can be mentioned. As the normal fibroblasts, for example, normal fibroblasts of ICR fetal mouse at the 12.5th day are exemplified. The feeder cells can be prepared by a conventional method. Commercially available products (mouse fibroblasts; Asahi Techno Glass Corporation, etc.) can be also utilized. It is preferable to use the feeder cells inactivated by the treatment with mitomycin C and the like.

3. Culture Medium

For the production (establishment and culture) of the rat ES cells of the present invention, a substantially serum free culture medium is used. The "substantially serum free" used herein means not to contain serum in an amount that rat ES cell loses the properties as an ES cell (e.g., becomes negative for alkaline phosphatase activity) due to the effect of serum. Specifically, it means that serum concentration is 10% or less, preferably 5% or less, more preferably 2% or less. More preferably, a serum-free medium is used. In this case, it is necessary to add a reagent to replace serum. Specifically, a serum replacement reagent (KSR: GibcoBRL) and the like are used. The serum replacement reagent is preferably used in a concentration of about 20%.

As regards rat leukemia inhibitory factor (rLIF), it is preferable to use a culture medium without rat LIF (rLIF) in the steps for the formation and separation of inner cell masses from blastocytes. On the other hand, in the steps after the formation of inner cell masses (including the culture and passage of established rat ES cells), an rLIF-containing culture medium is preferably used. As regards the concentration, it is preferable to add 100 units or more of rLIF per 1 ml of culture medium, and more preferable to add about 1000 units or more of rLIF. A commercially available product (Chemicon, Inc.) can be utilized as the rLIF.

As other components in the culture medium, components conventionally used for the culture of ES cells are appropriately contained in combination in the scope of one of ordinary skill in the art.

A specific composition of the culture medium is exemplified in the following.

1) Culture Medium for Rat ES Cell Establishment

A culture medium used in the steps from blastocysts to inner cell mass formation is referred to as "culture medium for rat ES cell establishment".

(Specific Example of Composition)

Dulbecco's modified Eagle medium/F12 (Ashahi Techno Glass, Tokyo, Japan) 380 ml
    0.2M L-glutamine 5 ml
    serum replacement reagent (KSR: Gibco BRL, Funakoshi, Tokyo, Japan) 100 ml
    non-essential amino acids (Gibco BRL, Funakoshi, Tokyo, Japan) 5 ml
    Antibiotic-Antimicrotics solution (Gibco BRL, Funakoshi, Tokyo, Japan) 5 ml
    100 mM Na-pyruvate 5 ml
    0.1M β mercaptoethanol 0.5 ml 2) Culture Medium for Rat ES Cells A culture medium used in the culture after inner cell mass formation (including culture of established rat ES cells) is referred to as "culture medium for rat ES cells".

(Specific Example of Composition)

Dulbecco's modified Eagle medium/F12 (Ashahi Techno Glass, Tokyo, Japan) 375 ml
    0.2M L-glutamine 5 ml
    serum replacement reagent (KSR: Gibco BRL, Funakoshi, Tokyo, Japan) 100 ml
    non-essential amino acids (Gibco BRL, Funakoshi, Tokyo, Japan) 5 ml
    100× nucleoside stock solution 5 ml
    (adenosine 4 mg, guanosine 4.25 mg, cytidine 3.65 mg, uridine 3.65 mg, thymidine 1.2 mg)
    Antibiotic-Antimicrotics solution (Gibco BRL, Funakoshi, Tokyo, Japan) 5 ml
    100 mM Na-pyruvate 5 ml
    0.1M β mercaptoethanol 0.5 ml
    1000 U rat leukemia inhibitory factor (rLIF)

Of these, rat leukemia inhibitory factor (rLIF) is preferably added and mixed just before use.

4. Culture Conditions

The temperature of cell culture in the production (establishment and culture) of rat ES cells of the present invention may be within the range of 35° C.-37.5° C., is preferably 37° C. The culture is carried out in a 5% $CO_2$ incubator used for a typical culture.

5. Method for Rat ES Cell Establishment

A specific example of the method for rat ES cell establishment of the present invention is shown in the following.

1) Oocyte (Embryo in Blastocyst Stage) Sampling

A rat for oocyte sampling is selected from the rat strains such as the aforementioned Wistar Kyoto (WKY) strain, Brown Norway (BN) strain, Goto-Kakizaki (GK) strain, SD strain, F344/Du (Fischer) strain, Wistar strain, Wistar Hannover strain and ACI strain. A rat within the range of 8 to 40 weeks old can be used, preferably a 10 to 20-week-old rat is used, more preferably a 10 to 12-week-old rat is used.

Oocyte sampling may be carried out by a conventional method known to one of ordinary skill in the art. Specifically, rats are naturally crossed, the female rat for oocyte sampling is sacrificed to excise an uterus about 3 days after vaginal plug detection. This uterus is perfused with a suitable medium to recover fertilized oocytes (embryos). The culture medium used herein includes, for example, mw medium (640.0 mg/100 ml NaCl, 35.6 mg/100 ml KCl, 16.2 mg/100 ml $KH_2PO_4$, 29.4 mg/100 ml $MgSO_4\cdot7H_2O$, 190.0 mg/100 ml $NaHCO_3$, 100.0 mg/100 ml glucose, 2.5 mg/100 ml Na-pyruvate, 46.0 mg/100 ml Ca-lactate, 5.0 mg/100 ml streptomycin, 7.5 mg/100 ml penicillin, 0.5% phenrol red (0.2 ml), 20 mM beta-ME (10 μl), 100 mM EDTA-2Na (10 μl), 300.0 mg/100 ml BSA), M2 medium (0.251 g/L calcium chloride-2$H_2O$, 0.143 g/L magnesium sulfate, 0.356 g/L potassium chloride, 0.162 g/L potassium phosphate, 5.532 g/L sodium chloride, 4.0 g/L albumin, 1.0 g/L D-glucose, 4.969 g/L HEPES, 0.01 g/L phenol red-Na, 0.036 g/L pyruvic acid-Na, 0.35 g/L sodium bicarbonate, 0.06 g/L penicillin G, 0.05 g/L streptomycin sulfate, 4.349 g/L D,L-lactic acid) and the like.

The recovered embryos are cultured in a culture medium such as mw medium, M2, M16, and the like.

By this culture, the development proceeds from fertilized oocytes (embryos) through moluras to blastocysts (embryos in blastocyst stage). To promote the development to this stage, the culture is typically performed in a 5% $CO_2$ incubator at 37° C. overnight. It can be confirmed by microscopic observations that the development has proceeded to blastocyst stage. Preferably, the development proceeds up to the late blastocyst stage.

2) Formation and Separation of Inner Cell Masses

The blastocysts obtained in the aforementioned 1) are confirmed microscopically, and zona pellucidas are removed. The zona pellucidas is removed using Acidic Tyrode (pH 2.5), hyaluronidase, pronase and the like. Then, feeder cells treated with mitomycin C are sown onto gelatin-coated culture dishes, 5-10 zona pellucida-removed rat blastocysts are transferred to each of the dishes, and the culture is started using a culture medium for rat ES cell establishment.

Between the 1st and 4th days of the culture, zona pellucida-removed rat blastocysts (late stage) adhere to the feeder cells. On 5-10 days after adhesion, an inner cell mass appeared from the blastocysts is mechanically separated using a 200 μl of pipette and the like. This separated inner cell mass is transferred to a sterilized tube and the like containing a culture medium for rat ES cell establishment, and dissociated until it becomes cell aggregates consisting of about 5-20 cells. At the time, the inner cell mass is not dissociated with a protease such as trypsin-EDTA and the like but is mechanically dissociated using a pipette and the like. In addition, it should be avoided to carry out the dissociation until single cells, and the dissociation is performed to the extent that cell aggregates consisting of about 5-20 cells remain as mentioned above. Being in a state that cell aggregates remain can be confirmed microscopically.

3) Establishment of ES Cells

In the gelatin-coated culture dishes wherein the feeder cells are sown, inner cell masses dissociated in the aforementioned 2) are cultured in a culture medium for rat ES cells. Primary ES cell colony usually appears between the 2nd and 4th days of the culture. The appearance of the primary ES cell colony can be confirmed by microscopic observations (the appeared ES cells are referred to as "primary ES cells"). By continuing the culture about 5-10 days thereafter, the primary ES cell colony becomes in a state capable of being passaged. The "state capable of being passaged" used herein means a state wherein the number of cells constituting the primary ES cell colony formed has reached approximately 200-600, and each cellular interval has become tight. While microscopically confirming that it has such morphology, the ES cell colony is separated using a 200 μl of pipette and the like. This separated ES cell colony is transferred to a sterilized tube and the like containing a culture medium for rat ES cells, and dissociated until it becomes cell aggregates consisting of about 5-20 cells. In this stage, it should also be avoided to carry out the dissociation until single cells, and the dissociation is performed to the extent that cell aggregates remain as mentioned above. Also in this stage, it is desirable that the cells are not dissociated with a protease such as trypsin-EDTA and the like but is mechanically dissociated. The dissociated ES cell colony is subjected to a primary culture (cells at passage 1) in a culture medium for rat ES cells in a gelatin-coated culture dish wherein the feeder cells are sown. An ES cell colony appears about 2-4 days and becomes in a state capable of being passaged about 5-10 days after the beginning of the culture.

The passage of the cells thereafter can be performed within the common knowledge of one of ordinary skill in the art, as long as maintaining a state that the cells are not made to single cells, namely a state that cell aggregates consisting of about 5-20 cells remain. It is desirable that cell dissociation is performed in a way minimizing a treatment with a protease such as trypsin-EDTA and the like and using a physical means. A specific example is shown in the following.

After removing the culture medium, the ES cell colony that has become capable of passaged in the above are washed with PBS(−) at room temperature and the entire surface thereof is coated with 2.5% trypsin previously incubated at 37° C. The amount of trypsin is preferably about 500 µl or more per 60 mm dish. The solution is removed immediately after the full coating with trypsin. When microscopically confirming a state that 70% or more of whole the ES cell colony is coming unstuck from the feeder cells, the trypsin treatment is immediately stopped. To stop the trypsin treatment herein, for example, it is easy to add a culture medium containing 10% fetal bovine serum. Alternatively, the treatment can be stopped by adding a large amount of serum-free culture medium and the like to dilute the trypsin concentration. Then, the ES cell colony is further unstuck mechanically using a 5 ml of pipette and the like, the cell suspension is centrifuged (for about 3 minutes at room temperature, 1000 rpm) to separate the cells and the culture medium and only the cells are recovered. The cells are suspended in a culture medium for rat ES cells, after microscopically confirming a state that the cells form aggregates of 5-20 cells rather than becoming fully single cells, the cells are transferred to a gelatin-coated culture dishes wherein the feeder cells are sown and cultured (cells at passage 2).

After that, since the cells become in a state capable of passaged every about 5-10 days, they can be passaged and cultured by the same subculture method as in the passage of the cells at passage 1 (passage to the cells at passage 2).

It is deemed that the ES cell is established when the numbers of the cell aggregates and the cells constituting the cell aggregates become constant. Specifically, the cell at passage 3 or later, desirably passage 5 or later can be deemed as the established rat ES cell. When established rat ES cells are supplied as a commercial product, cells at passage 3 or later, preferably passage 5 or later, more preferably passage 10 or later are the objects for commercialization, in order to maintain a stable supply from a single line.

6. Rat ES Cell of the Present Invention

The rat ES cell of the present invention is characterized by having the following properties (a)-(j):
(a) expressing Oct3/4 gene and Nanog gene,
(b) positive for alkaline phosphatase activity,
(c) having an embryoid body forming ability,
(d) expressing SSEA (Stage-Specific Embryonic Antigen)-1 and SSEA-4,
(e) having the same number of chromosomes as does a normal rat cell,
(f) capable of being subcultured and holding the undifferentiated state,
(g) having in vitro pluripotency,
(h) having a potential to differentiate to cells of three embryonic germ lineages,
(i) having teratoma formation ability, and
(j) having an ability to produce a chimeric rat.

The present invention provides a rat ES cell retaining all the properties as an ES cell shown in the aforementioned (a)-(j) for the first time. It can be analyzed by the following methods that the established rat ES cell retains the properties as an ES cell, that is the properties as an ES cell maintaining an undifferentiated state (totipotency).

1) Expression of Markers for Undifferentiated State

Oct3/4 (Okamoto, K. et al., *Cell*, 60: 461-472 (1990), Scholer, H. R. et al., *EMBO J.* 9: 2185-2195 (1990)) and Nanog (Mitsui, K. et al., *Cell*, 113: 631-642 (2003), Chambers, I. et al., *Cell*, 113: 643-655 (2003)) are known as critical factors defining a cell as an ES cell. The expression of these genes can be determined by RT-PCR using rat Oct3/4- and Nanog-specific primers. As the rat Oct3/4- and Nanog-specific primers used herein, the primers described in the Examples (Oct3/4: 5'-ATGGACTACCCAGAAC-CCCAG-3' (SEQ ID NO:3), 5'-TTACAGGAGCTGCAGT-TATAC-3' (SEQ ID NO:4), Nanog: 5'-TAGCCCTGATTCT-TCTAGCA-3' (SEQ ID NO:5), 5'-TTTGCTGCAACGGCACATAA-3' (SEQ ID NO:6)) are exemplified.

2) Alkaline Phosphatase Activity

An undifferentiated ES cell expresses an alkaline phosphatase in large amounts. The expression of the alkaline phosphatase can be easily determined using various commercially available alkaline phosphatase detection kits. The detection kits include, for example, ALP tissue staining kit (Sigma) and Vector Red Alkaline Phosphatase Substrate Kit I (Funakoshi) and the like.

3) Embryoid Body Forming Ability

It is known that an embryoid body is formed by culturing an ES cell using a non-coated culture dish under conditions without feeder cells and LIF (Roy, S. et al., *Mol. Cell. Biol.*, 18: 3947-3955 (1998)). The embryoid body formation can be confirmed by microscopic observations of the appearance of a spherical body formed by cell aggregation after rat ES cells are cultured using a culture medium for rat ES cells without LIF in a non-coated culture dish for about 7 days to 14 days.

4) Expression of Cell Surface Antigen

As one of the indexes identifying the differentiation of pluripotent stem cells including ES cell, the detection of cell surface antigens whose expression amounts change specifically in the differentiation stage can be mentioned. The rat ES cell of the present invention expresses SSEA (stage-specific embryonic antigen)-1 and SSEA-4. The expression of the cell surface markers can be evaluated by an immunostaining using ES Cell Characterization Kit (Funakoshi).

5) Chromosome Number

It can be confirmed by analyzing the chromosome number by G-banding method (Sumner, A. T., *Cancer Genet Cytogenet.* 6: 59-87 (1982)) that the established rat ES cell is a normal ES cell maintaining the chromosome number (2n=42) of rat from which it originates.

6) Maintenance of Undifferentiated State

The established ES cell can be subcultured with maintenance of undifferentiated state. The rat ES cell established by the present invention has a superior characteristic that it can be subcultured until at least 35 passages. The maintenance of undifferentiated state can be confirmed by performing a subculture according to the subculture method of the rat ES cell of the present invention (the aftermentioned 7.), and determining the aforementioned alkaline phosphatase activity and the like.

7) Pluripotency

ES cell spontaneously differentiates into various cells through an embryoid body by culturing it under conditions without feeder cells and LIF. This property of ES cell can be observed by forming an embryoid body by the method described in the aforementioned 3), then transferring the embryoid body to a gelatin-coated culture dish and culturing it for about 7-14 days. The appearance of neuron-like cell, adipose-like cell or epidermoid cell or the like can be confirmed by the characteristic morphology of the each cell.

8) Differentiation Potential to Cells of Three Embryonic Germ Lineages

ES cell has a potential differentiating to cells of three embryonic germ (endoderm, mesoderm, ectoderm) lineages. This property of ES cell can be confirmed by extracting RNA from an embryoid body (embryoid body wherein a myocardium-like cell appears) formed by the method described in the aforementioned 3), and analyzing the expression of each marker gene for ectodermal cell (e.g., neuron), mesodermal cell (e.g., cardiomyocyte) and endodermal cell (e.g., hepatocyte) by RT-PCR.

The neuron markers include Nestin, TUJ1 (beta3-tublin), MSI-1 (musashi-1), GFAP (glial fibrillary acidic proteins alpha) and the like. The cardiomyocyte markers include CCC (cardiac dihydropyridine-sensitive calcium channel protein), ANF (atrial natriuretic factor), KvLQT1 and the like. The hepatocyte markers include ALB (albumin), TDO (tryptophan 2,3-dioxygenase), TAT (tyrosine aminotransferase), G6P (glucose-6-phosphatase) and the like.

9) Ability of Teratoma Formation

The transplantation of ES cells to a homologous or innate immunodeficient heterologous animal can lead to a teratoma formation. The teratoma used herein is the designation of a mixed tumor wherein various tissues derived from three embryonic germs, endoderm, mesoderm and ectoderm, are randomly present in a tumor. The formation of the teratoma can be confirmed by transplanting rat ES cells to the subdermic and the like of a homologous animal or a heterologous animal with a primary immune deficiency, and macroscopically observing the presence of a bunchy body after several months. It can be confirmed that the teratoma formed has three embryonic germ structures by sectioning the excised teratoma, staining with hematoxylin/eosin and observing the morphology of the tissues and cells microscopically.

10) Chimeric Rat-Producing Ability

A chimeric rat can be produced by introducing ES cells into a homologous or heterologous rat. The production of the chimeric rat can be carried out by, for example, the following method.

To facilitate confirmation of the production of the chimeric rat, a marker gene (e.g., GFP, β-gal, luciferase, etc.) may be previously introduced into the rat ES cell of the present invention. Specifically, a recombinant rat ES cell incorporating a vector containing such marker gene in the ES cell chromosome is established by incorporating the aforementioned vector into the rat ES cell chromosome by an electroporation method and the like, followed by selection in a culture medium supplemented with a drug. The recombinant rat ES cells are, for example, transplanted into a blastocoele of a rat blastocyst or into morula stage or 16-cell stage embryo by a microscopic manipulation and developed with an inner cell mass or as a part of an inner cell mass (microinjection method: Gordon J. W. et al., *Proc. Natl. Acad. Sci. USA.*, 77: 7380-7384 (1980)). Alternatively, zona pellucidas are removed from two 8-cell embryos and the embryos are co-cultured with the aforementioned recombinant rat ES cells to form an aggregate. When the resulting aggregate is cultivated, one blastocyst is obtained (cell aggregate method: Dvorak P. et al., *Int. J. Dev. Biol.*, 39: 645-652 (1995)). The embryo (egg for transplantation) obtained above is transplanted in the uterus of a pseudopregnant female rat prepared by natural crossbreeding with a male rat after vasoligation treatment and developed, whereby a chimeric rat can be produced.

That the obtained chimeric rat has cells and tissues derived from an ES cell, or an established rat ES cell has a chimeric rat-producing ability can be confirmed by a general method known to those of ordinary skill in the art. For example, it can be confirmed by genomic PCR using genomic DNA extracted from various tissues of chimeric rat as a template and marker gene (marker gene introduced into ES cell)-specific primers. Moreover, differentiation of ES cell to the cell of each tissue lineage can be confirmed, for example, by sectioning each tissue of a chimeric rat, and detecting the presence of a marker gene expression product (marker protein) based on the properties of the marker protein used.

11) Differentiation by Culture in the Presence of Serum

Moreover, the rat ES cell of the present invention has a property that it differentiates by culture in the presence of 20% serum. Preferably, the rat ES cell of the present invention differentiates by culture in the presence of 10% serum, more preferably by culture in the presence of 5% serum. The differentiation of rat ES cell can be confirmed by the disappearance of alkaline phosphatase activity, or disappearance of expression of ES cell marker genes such as Oct3/4, Nanog and the like.

7. Subculture Method of Rat ES Cell

The rat ES cell of the present invention can be subcultured while maintaining an undifferentiated state. The rat ES cell of the present invention can be passaged within the range of technical common knowledge of those of ordinary skill in the art, as long as the cells are maintained in a non-single-cell state, namely, a state of cell aggregate consisting of about 5-20 cells. It is desirable that a treatment by proteinase such as trypsin-EDTA and the like is applied as little as possible, and cell dissociation is carried out by a physical means. Specific examples are shown in the following.

After removing the culture medium, the established ES rat cells that have become capable of being passaged are washed with PBS(-) at room temperature and the entire surface thereof is coated with 2.5% trypsin previously incubated at 37° C. The amount of trypsin is preferably about 500 μl or more per 60 mm dish. The solution is removed immediately after the full coating with trypsin. When microscopically confirming a state that 70% or more of whole the ES cell colony is coming unstuck from the feeder cells, the trypsin treatment is immediately stopped. To stop the trypsin treatment herein, for example, it is easy to add a culture medium containing 10% fetal bovine serum. Alternatively, the treatment can be stopped by adding a large amount of serum-free culture medium and the like to dilute the trypsin concentration. Then, the ES cell colony is further unstuck mechanically using a 5 ml of pipette and the like, the cell suspension is centrifuged (for about 3 minutes at room temperature, 1000 rpm) to separate the cells and the culture medium and only the cells are recovered. The cells are suspended in a culture medium, after microscopically confirming a state that the cells form aggregates of 5-20 cells rather than becoming fully single cells, the cells are transferred to a gelatin-coated culture dishes wherein the feeder cells are sown and cultured. Thereafter, the passageable state occurs every about 5-10 days, and subculture is conducted in the same manner.

For the culture of passaged cells, a culture medium substantially free of serum is used. The "substantially free of serum" used herein means not to contain serum in an amount that rat ES cell loses the properties as an ES cell (e.g., becomes negative for alkaline phosphatase activity) due to the effect of serum. Specifically, it means that serum concentration is 10% or less, preferably 5% or less, more preferably 2% or less. More preferably, a serum-free medium is used. In this case, it is necessary to add a reagent to replace serum. Specifically, a culture medium containing a serum replacement reagent (KSR: GibcoBRL) and the like are used. The serum replacement reagent is preferably used in a concentration of about 20%.

The culture medium to be used for the culture of the aforementioned passaged cells desirably contains rLIF. As the concentration of rLIF, rLIF is preferably added at not less than 100 units, and more preferably about 1000 units, or not less than that, per 1 ml of the culture medium.

As mentioned above, a culture medium for subculture of the rat ES cell of the present invention preferably contains a serum replacement reagent and rLIF, and the culture medium for rat ES cells described in the aforementioned 3.-2) is used effectively.

8. Rat ES Cell Culture Kit

The present invention provides a culture kit for cultivating the rat ES cell of the present invention. To be specific, the present invention provides a rat ES cell culture kit containing a serum replacement reagent (KSR) and rLIF as components. While the serum replacement reagent and rLIF in a mixture may be sealed in a single container, they are each preferably sealed in a separate container. As KSR, one manufactured by Gibco BRL can be used, and as rLIF, one manufactured by Chemicon can be used.

The aforementioned kit can further contain a rat ES cell of the present invention as a component. When the rat ES cell of the present invention is supplied as a commercial product, the cell at passage 3 or later, preferably passage 5 or later, more preferably passage 10 or later are the objects for commercialization. While the rat ES cell can be commercialized by itself, it may be commercialized as one component of the culture kit of the present invention as mentioned above.

The aforementioned kit can further contain a feeder cell as a component. The feeder cell may be one derived from any species available to one of ordinary skill in the art, and is preferably normal fibroblast rather than an established line of feeder cell. Specifically, primary cultured cells of mouse embryonic fibroblasts (normal fibroblasts) between the 12th and 16th days of pregnancy can be mentioned. As the normal fibroblasts, for example, normal fibroblasts of ICR fetal mouse at the 12.5th day are exemplified. The feeder cells can be prepared by a conventional method. Mouse embryonic fibroblasts (Asahi Techno Glass Corporation), etc. can be also utilized.

The production methods (establishment method, subculture method) of ES cell, and culture medium and culture kit of ES cell as mentioned above are applicable to rat ES cell as well as other animal species (except mouse).

Mouse ES cell colony rises like a dome, with generally indefinite cell boundary between the adjacent cells. It is glossy. In contrast, the colony of primate ES cells is flattened, with no gloss as observed in mouse ES cell. Moreover, the boundary between cells is clearer than in mouse ES cells. It has been clarified that the rat ES cells established in the present invention form a flat colony, free of high gloss possessed by mouse ES cell, and show morphology closer to that of primate ES cell than mouse. Therefore, the production methods (establishment method, subculture method) of ES cell of the present invention, and culture medium and culture kit of ES cell as mentioned above are applicable to ES cell of primates.

9. Cell Obtained by Differentiation Induction of Rat ES Cell

The present invention provides a differentiation induction method of rat ES cell of the present invention, and a cell obtained by differentiation induction.

As known in mouse and human ES cells, ES cell can be induced to differentiate into various cells by culturing ES cell under the conditions free of feeder cell and LIF (Roy. S. et al., *Mol. Cell. Biol.*, 18: 3947-3955 (1998)). In addition, it can be induced to differentiate into various cells by the action of retinoic acid, cell growth factors, glucocorticoids and the like (Kawamorita M. et al., *Hum. Cell.*, 15: 178-182 (2002)). Moreover, differentiation induction can be performed with an extracellular substrate. Accordingly, similar differentiation induction can be performed by cultivating the rat ES cell of the present invention under the aforementioned conditions. As the cells obtained here by differentiation induction of ES cell, for example, neuron, hematopoietic cell lineage, hepatocyte, vascular endothelial cell, cardiomyocyte and the like can be mentioned.

The cells obtained by differentiation induction of ES cell are useful, for example, as the cells for transplantation in an experimental model for a transplantation treatment. In addition, the differentiated cell can also be used effectively for examining the influence of exposure of the cell to nucleic acid, protein or carcinogen, environmental mutagen substance and the like. To be specific, the influence on the cell can be examined based on the biological indices such as genetic or epigenetic changes of the cell, cell transformation, colony formation ability in soft agar medium, changes of canceration indices including infiltration ability, changes of metabolic function, changes of physiological function, biochemical changes and the like, by the addition of the aforementioned substances.

10. Substance Derived from Rat ES Cell

By establishing the rat ES cell in the present invention, not only rat ES cell but also various substances derived therefrom (e.g., cDNA library prepared from mRNA and genomic library of the established rat ES cell, or cell extract of rat ES cell and the like) can be provided. Various substances derived from the ES cell of the present invention can be used effectively for the research of regenerative medicine and study of molecular level expression analysis, drug discovery research and safety evaluation test and the like.

As used herein, the cDNA library can be produced using RNA extracted from the rat ES cell of the present invention as a template and a commercially available cDNA library construction kit (e.g., CloneMiner cDNA Library Construction Kit (Invitrogen), Creator SMART cDNA Library Construction Kit (BD Biosciences) etc.) and the like. In addition, a genomic library can be produced by a conventional method by reference to basic books such as *Molecular Cloning, A Laboratory Manual.*, T. Maniatis et al. ed., 2nd edition (1989), Cold Spring Harbor Laboratory and the like. In addition, the cell extract derived from ES cell can be prepared by disrupting the cell by a conventional method, centrifugation in the presence of a protease inhibitor and the like.

11. Screening Method for Tissue or Cell Differentiation Inducer

The present invention provides a screening method for a tissue or cell differentiation inducer, which comprises the following (i)-(iii):

(i) a step for contacting a test substance with the rat ES cell of the present invention, (ii) a step for evaluating the presence or absence, or the extent of differentiation of rat ES cell, and (iii) a step for judging whether or not the test substance is a substance associated with differentiation induction, based on the evaluation results of the above-mentioned (ii).

While the test substance to be subjected to the screening in the aforementioned step (i) is not limited, nucleic acid, peptide, protein, organic compound, inorganic compound and the like can be mentioned. The aforementioned screening is specifically performed by bringing the test substance or a sample containing the substance (test sample) in contact with the rat ES cell. As such test sample, cell extract, gene (genomic, cDNA) library, RNAi library, antisense nucleic acid, synthetic low-molecular-weight compound, synthetic peptide, natural compound and the like can be mentioned. These test samples and test substances are contacted in a form permitting uptake into the rat ES cell. For example, when the test sample is a nucleic acid, it is introduced into the ES cell by microinjection, calcium phosphate, DEAE-dextran or a lipid for gene introduction.

The conditions under which the rat ES cell is brought into contact with the test substance are not particularly limited as long as the cell is not killed and the culture conditions (temperature, pH, composition of culture medium and the like) are suitable for uptake of the test substance. Preferably, the aforementioned test substance is added to the cultured rat ES cell under the conditions suitable for differentiation induction, namely, under the conditions free of feeder cell and LIF.

In the subsequent step (ii), the presence or absence, or the extent of differentiation of rat ES cell is evaluated, and in (iii), whether or not the test substance is related to the differentiation induction is judged based on the evaluation results. Differentiation of the rat ES cell into a desired tissue or cell can be evaluated, for example, using, as an index, a marker that expresses in a desired tissue or cell. As the marker of the desired tissue or cell, a tissue- or cell-specific antigen can be mentioned. Specifically, as the marker, for example, neuron-specific enolase, glial fibrillary acidic protein, Nestin and the like can be mentioned as a neural cell marker, S-100 protein, tartaric acid resistant acid phosphatase and the like can be mentioned as a cartilage marker. As a muscle marker, desmin, muscle-specific actin and the like can be mentioned. Such tissue or cell specific marker can be detected by ELISA, immunostaining and the like, using an antibody against the marker. It is also possible to detect expression of the marker gene by RT-PCR and the like.

12. Screening Method for Substance Acting on Tissue or Cell Differentiation Induction The present invention provides a screening method of a substance acting on the differentiation induction of tissue or cell, which comprises the following steps (I)-(III):

(I) a step for contacting a test substance with the rat ES cell of the present invention, (II) a step for culturing the rat ES cell of the aforementioned (I) under the conditions allowing differentiation induction of the ES cell, and evaluating the presence or absence or the extent of the differentiation thereof, and (III) a step for judging whether or not the test substance is a substance acting on the differentiation induction, based on the evaluation results of the above-mentioned (II).

As mentioned above, ES cell can be induced to differentiate into various cells by culturing ES cell under the conditions free of feeder cell and LIF (Roy. S. et al., *Mol. Cell. Biol.,* 18: 3947-3955 (1998)). In addition, it can be induced to differentiate into various cells by the action of retinoic acid, growth factors, glucocorticoids and the like (Kawamorita M. et al., *Hum. Cell.,* 15: 178-182 (2002)). Moreover, differentiation induction can be performed with an extracellular substrate. Addition of a test compound (e.g., pharmaceutical product such as anti-cancer agent and the like, environmental mutagen and the like) to the culture system followed by culture enables to evaluate an influence of the test substance on normal differentiation. The screening can be applied to, for example, the study of the side effects of the pharmaceutical product under development and the like.

As the test substance subjected to the screening in step (I), those similar to the substance of the aforementioned 11. can be mentioned. For contact of the test substance with the rat ES cell, the test substance may be brought into contact with the rat ES cell of the present invention and then cultured under the conditions for the differentiation induction of ES cell, or the rat ES cell may be cultured under the conditions for the differentiation induction and thereafter contacted with the test substance.

As the culture under the conditions for differentiation induction, under the aforementioned culture conditions free of feeder cell and LIF, culture conditions where retinoic acid, growth factors, glucocorticoids, extracellular substrate and the like are added to the culture medium and the like can be mentioned. During the culture process or after the culture under the conditions for differentiation induction, an influence of the test substance on the differentiation of the rat ES cell is evaluated. The evaluation is desirably conducted based on the comparison of the extent of the differentiation in the object cell without an action of the test substance. To be specific, for example, differentiation to functional mature hepatocyte is induced by the addition of a hepatocyte differentiation inducer (JP 2004-59705 A) to a culture medium, and can be evaluated using a hepatocyte-specifically expressing gene (albumin, tryptophan 2,3-dioxygenase etc.) and the like as an index.

13. Genetically Modified Rat

The rat ES cell of the present invention can be used for the preparation of a genetically modified rat.

Rat is a mammal having an experimentally suitable size of about 10 times the size of mouse, and is advantageous in that (1) drug administration into the blood vessel in the cell is easy, (2) a surgical or transplantation test can be performed, (3) a large amount of tissue can be collected and the like. While many human disease model rats have been conventionally developed and discovered, since rat ES cell was not established, preparation of a genetically modified rat, particularly a genetically modified rat requiring gene targeting such as knockout rat and knockin rat, has been practically impossible. The rat ES cell of the present invention has first enabled preparation of such a genetically modified rat. By the provision of the rat ES cell of the present invention, the genetically modified rat can be produced by the technique well known to those of ordinary skill in the art.

Here, the "genetically modified rat" means any genetically modified rat known to those of ordinary skill in the art, such as chimeric rat, knockout rat, knockin rat, transgenic rat and knockdown rat.

The aforementioned genetically modified rat can be produced by a process including the following steps (X)-(Z):
(X) a step for introducing a desired gene into the rat ES cell of the present invention,
(Y) a step for preparing an oocyte for transplantation comprising the rat ES cell into which the gene was introduced, and
(Z) a step for transferring the oocyte for transplantation into a pseudopregnant female rat to produce an offspring rat.

Knockout rat means a mutant rat wherein a target gene has been artificially destroyed, and is also called a gene targeting rat. A knockout rat can be prepared, for example, according to a preparation method of a knockout mouse as described in Donehower, A. L. et al. *Nature*, 356: 215-221 (1992) and the like. Briefly, a vector for homologous recombination (targeting vector) is constructed based on the genomic DNA sequence of a target gene. At this time, a drug resistant gene such as a G418 resistant gene, a hygromycin resistant gene and the like is incorporated as a marker gene for selection of a recombinant clone. The constructed targeting vector is introduced into the rat ES cell by an electroporation method and the like. From the obtained transfected cells, a colony in which a homologous recombination has occurred is selected. The homologously recombined rat ES cell thus obtained is, for example, transplanted into a blastocoele of a rat blastocyst or into morula stage or 16-cell stage embryo by a microscopic manipulation and developed with an inner cell mass or as a part of an inner cell mass (microinjection method: Gordon J. W. et al., *Proc. Natl. Acad. Sci. USA.*, 77: 7380-7384 (1980)). Alternatively, zona pellucidas are removed from two 8-cell embryos and the embryos are co-cultured with the aforementioned recombinant rat ES cells to form an aggregate. When the resulting aggregate is cultivated, one blastocyst is obtained (cell aggregate method: Dvorak P. et al., *Int. J. Dev. Biol.*, 39: 645-652 (1995)). The embryo (oocyte for transplantation) obtained above is transplanted in the uterus of a pseudopregnant female rat prepared by natural crossbreeding with a male rat after vasoligation treatment and developed, whereby a chimeric rat can be produced. By crossing the chimeric rat with a wild-type rat, a heterozygous knockout rat can be produced, and when heterozygous knockout rats are crossed, a homozygous knockout rat can be produced.

The category of the aforementioned knockout rat includes a conditional knockout rat. The conditional knockout means a system to site-specifically or time-specifically knockout a gene utilizing a Cre/loxP system or a FLP/FRT system. To be specific, a gene to be targeted is substituted by a gene flanked by loxP sequences or FRT sequences, and Cre or FLP protein is supplied to cleave the gene flanked by the aforementioned loxP sequences or FRT sequences (Sternberg N., et al., *J. Mol. Biol.*, 150: 487-507 (1981)).

Knockin rat means a mutant rat in which an artificially prepared exogenous gene having homology to a target gene has been introduced into the site thereof. The target gene may or may not be destroyed. For example, to monitor gene expression, a marker gene such as a lacZ gene, a GFP gene and the like may be introduced or a gene may be exchanged to one in which a mutation has been introduced.

The knockin rat can be produced, for example, according to a preparation method of a knockin mouse as described in Pewzner-Jung, Y. et al., *J. Immunol.*, 161: 4634-4645 (1998) and the like. Basically, the rat can be produced by the same principle as in the aforementioned knockout rat.

Transgenic rat means a rat in which a foreign gene has been artificially introduced. A transgenic animal is conventionally prepared by injection of a desired gene into the male pronucleus of a fertilized oocyte by microscopic manipulation. Therefore, the need for the rat ES cell of the present invention is not as high as in the case of the aforementioned knockout rat and knockin rat. However, the rat ES cell of the present invention is effectively used for increasing the introduction efficiency and individual preparation efficiency.

The transgenic rat can be produced, for example, according to the preparation method of transgenic mouse as described in Yamamoto H. et al., *Cancer Res.*, 62: 1641-1647 (2002) and the like. That is, ES cell is sacked with a glass pipette to hold thereon, and an exogenous target gene solution is directly injected into the nucleus from the other end using a thin and sharp glass pipette (tip not more than 2 μm). The ES cell, into which the solution has been injected, is transferred to a culture system. A strain incorporating the gene is established, a fertilized oocyte (morula stage or blastocyst stage embryo) of mouse is sacked with a glass pipette to hold thereon, the established ES cell is injected into the fertilized oocyte with a glass pipette, the oocyte is cultured in a test tube, developed to a certain level, and returned to the oviduct or uterus of a pseudopregnant female mouse to produce an offspring mouse.

The category of the aforementioned transgenic rat includes a conditional transgenic rat. The conditional transgenic means a system to site-specifically or time-specifically express a gene utilizing a Cre/loxP system or a FLP/FRT system. To be specific, a drug resistant gene is flanked by loxP sequences or FRT sequences, and Cre or FLP protein is supplied to cleave the gene flanked by the loxP sequences or FRT sequences, whereby the object gene is expressed (Sternberg, N., et al., *J. Mol. Biol.*, 150: 487-507 (1981)).

Knockdown rat means a rat, into which a short double strand RNA (siRNA), which is an intermediate for RNAi, or antisense nucleic acid has been artificially introduced and expressed, and expression of the target gene is suppressed by the action of the siRNA or antisense nucleic acid. Preparation of such knockdown animal has been enabled based on the establishment of an expression system of siRNA by a vector system (*Science* 296: 550-553 (2002), *Nature Biotech.* 20: 500-505 (2002) etc.).

The knockdown rat can be produced, for example, according to the method described in Tiscornia, G. et al., *Proc. Natl. Acad. Sci. USA*. 100: 1844-1848 (2003) and the like. Basically, the rat can be produced by the same principle as in the aforementioned transgenic rat.

The present invention also provides a genetically modified rat produced by the above operation. Here, "genetically modified rat" means any genetically modified rat known to those of ordinary skill in the art, as mentioned above, such as chimeric rat, knockout rat, knockin rat, transgenic rat and knockdown rat.

EXAMPLES

The present invention is explained in detail in the following by referring to Examples, which are not to be construed as limitative.

Example 1

Establishment of Rat ES Cell
1) Oocyte Sampling

A female WKY/N (Wistar Kyoto strain, Charles River Laboratories Japan, 10-week-old or older) was naturally crossbred, at 3 days after vaginal plug confirmation, the female rat for oocyte sampling was sacrificed and the uterus was excised. After perfusing with mw medium (640.0 mg/100 ml, NaCl, 35.6 mg/100 ml KCl, 16.2 mg/100 ml $KH_2PO_4$, 29.4 mg/100 ml $MgSO_4$-$7H_2O$, 190.0 mg/100 ml $NaHCO_3$, 100.0 mg/100 ml Glucose, 2.5 mg/100 ml Na-pyruvate, 46.0 mg/100 ml Ca-lactate, 5.0 mg/100 ml Streptomycin, 7.5 mg/100 ml Penicillin, 0.5% phenrol red (0.2 ml), 20 mM beta-ME (10 µl), 100 mM EDTA-2Na (10 µl), 300.0 mg/100 ml BSA), the embryo was recovered, and developed to become blastocyst (late stage) in 5% $CO_2$ incubator (FIG. 1). In the establishment of rat ES cell, since oocytes in the late stage of blastocyst showed the highest establishment (inner cell mass formation) efficiency, the oocyte in the late stage of blastocyst was used as shown above.

2) Preparation of Feeder Cell

Figure 2:
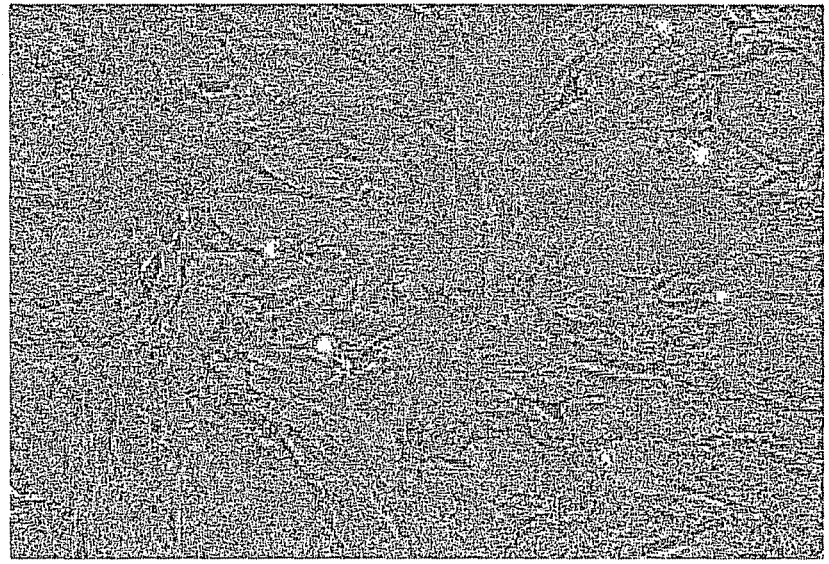
FIG. 2 is a photograph of the normal mouse embryonic fibroblasts (feeder cells) treated with mitomycin C used for the establishment of rat ES cells.

As a feeder cell to be used for the establishment and culture of rat ES cell, normal fibroblast of fetal mouse ICR at 12.5 days treated with mitomycin C was used (FIG. 2). Before use, a cryopreserved feeder cell was thawed one day before use, and cultured using STO medium (DMEM 450 ml, FBS 50 ml, Antibiotic-Antimicrotics solution 5 ml) and a gelatin-coated culture dish (Iwaki, Tokyo, Japan).

3) Consideration of Culture Medium for Rat ES Cell Establishment and Culture Medium for Rat ES Cells (1) Consideration of LIF Addition An inner cell mass is formed from the rat blastocyst prepared in the aforementioned 1), an ES cell colony is formed from the inner cell mass, and a stabilized rat ES cell is finally established. The culture medium to be used for a series of these steps was considered.

The necessity of addition of a rat leukemia inhibitory factor (rLIF) to a culture medium during the step of formation of an inner cell mass from rat blastocyst was first considered. Various concentrations (0-5000 units) of rLIF (Chemicon) were added during the step of formation of an inner cell mass from rat blastocyst, and the blastocyst was cultured. The number of the inner cell masses formed thereafter and the number of the primary ES cells were observed. As a result, inner cell mass was formed efficiently without rLIF, which was shown to have varied depending on the concentration of rLIF added. From such results, LIF-free culture medium was used until the end of the stage of inner cell mass formation.

Figure 3:
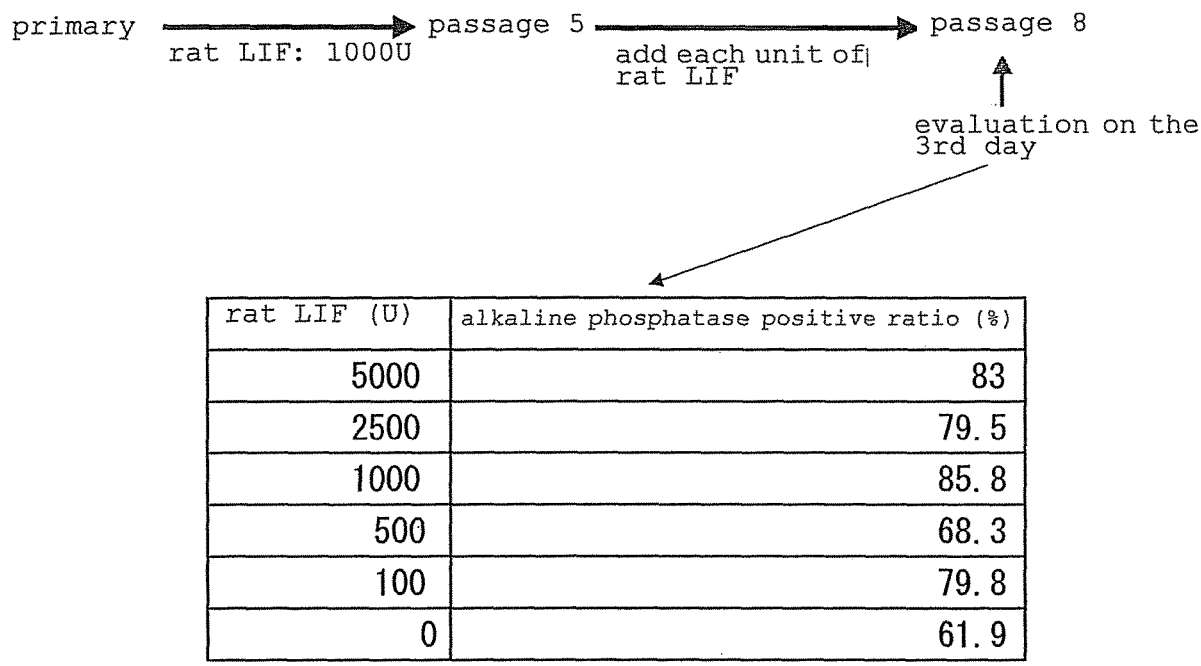
FIG. 3 is a drawing showing the results of the investigation on the necessity of the addition of rat LIF after the establishment of rat ES cells. At beginning the cells are at passage 5. Upon 3 passages using culture media supplemented with each concentration of rLIF from the same culture dish, the positive ratios of alkaline phosphatase activity were examined, which results are shown.

Then, whether or not to add rLIF during the stage of from after the inner cell mass formation to establishment of rat ES cell was considered. As a result of culture in a culture medium containing rLIF (1000 units) after the inner cell mass formation and separation, ES cell could be established from the inner cell mass at a rate of not less than about 50%. Furthermore, the necessity of addition of rLIF after rat ES cell establishment was also examined. The rat ES cell was cultured to passage 5 in a culture medium containing 1000 units of rLIF, various concentrations of rLIF was added to the rat ES cells (passage 5), and the cells were subcultured for 3 passages. An ability of the cell to maintain the undifferentiated state was determined by alkaline phosphatase positive ratio (%) measurement (method of alkaline phosphatase activity measurement is described in Example 2). As a result, it was clarified that, for the maintenance of an undifferentiated state-maintaining ability, addition of not less than 100 units of rLIF is preferable, and addition of not less than about 1000 units or more, per 1 ml of culture medium is more preferable (FIG. 3). From these results, an rLIF-supplemented culture medium was used after the inner cell mass formation.

(2) Consideration of Serum Addition

Conventionally, fetal bovine serum (FBS) is used for culturing ES cells. Whether or not to add FBS for rat ES cell establishment was examined.

Figure 4:
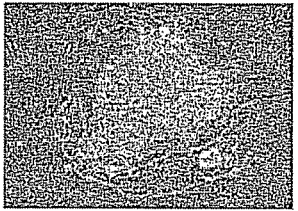
FIG. 4 shows photographs that show the results of study on the presence and absence of serum in a culture medium. (A) is a photograph showing the formation of a rat inner cell mass when 20% serum replacement reagent (KSR) is used, (B) is a photograph showing the formation of a rat inner cell mass when 20% fetal bovine serum is used, (C) is a photograph of the morphology of the culture when the rat inner cell mass produced using 20% serum replacement reagent (KSR) is cultured using a culture medium for rat ES cells supplemented with 20% serum replacement reagent (KSR) and feeder cells, and (D) is a photograph of the morphology of the culture when the rat inner cell mass produced using 20% fetal bovine serum is cultured using a culture medium for rat ES cells supplemented with 20% fetal bovine serum and feeder cells, respectively.

To be specific, inner cell mass formation ability and formation rate with or without (serum replacement reagent was used) addition of 20% FBS in the stage of forming inner cell mass from rat blastocyst were examined. In addition, maintenance or non-maintenance of the undifferentiated state-maintaining ability of ES cells at passage 1 following primary culture was also examined. The maintenance or non-maintenance of the undifferentiated state-maintaining ability was judged by the presence or absence of the alkaline phosphatase activity and embryoid body formation ability. As a result, when FBS was added, most of them were differentiated into multinuclear cells, without forming an inner cell mass (even if the mass is formed, it does not sufficiently grow to a size separable from trophoblast). The primary cultured ES cells were negative for the alkaline phosphatase activity, which is an index of undifferentiated state, and did not form a colony or an embryoid body. In contrast, when a serum replacement reagent (KSR) was used instead of the serum, an inner cell mass capable of being picked up from the rat blastocyst was formed, the alkaline phosphatase activity was also positive in the primary cultured ES cells, and a colony and an embryoid body were formed (FIG. 4). From the results, it has been clarified that KSR is superior to FBS in rat ES cell establishment. When the FBS concentration was 5% or 10%, the results were similar to those in the aforementioned 20% FBS.

(3) Composition of Culture Medium

Based on the examination results of the above-mentioned (1) and (2), a culture medium having the following composition was used for establishing the rat ES cell.

Culture Medium for Rat ES Cell Establishment

It is a culture medium to be used in the stage of forming inner cell mass from blastocyst.

Dulbecco's modified Eagle medium/F12 (Asahi Techno Glass, Tokyo, Japan) 380 ml 0.2M L-glutamine 5 ml serum replacement reagent (KSR: Gibco BRL, Funakoshi, Tokyo, Japan) 100 ml non-essential amino acids (Gibco BRL, Funakoshi, Tokyo, Japan) 5 ml Antibiotic-Antimicrotics solution (Gibco BRL, Funakoshi, Tokyo, Japan) 5 ml 100 mM Na-pyruvate 5 ml 0.1M β mercaptoethanol 0.5 ml Culture Medium for Rat ES Cell It is a culture medium to be used for culture after formation of inner cell mass.

Dulbecco's modified Eagle medium/F12 (Asahi Techno Glass, Tokyo, Japan) 375 ml 0.2M L-glutamine 5 ml serum replacement reagent (KSR: Gibco BRL, Funakoshi, Tokyo, Japan) 100 ml non-essential amino acids (Gibco BRL, Funakoshi, Tokyo, Japan) 5 ml 100-fold nucleoside stock solution 5 ml (adenosine 4 mg, guanosine 4.25 mg, cytidine 3.65 mg, uridine 3.65 mg, thymidine 1.2 mg)

Antibiotic-Antimicrotics solution (Gibco BRL, Funakoshi, Tokyo, Japan) 5 ml 100 mM Na-pyruvate 5 ml 0.1M β mercaptoethanol 0.5 ml 1000 U rat leukemia inhibitory factor 4) Consideration of Isolation Method of Rat ES Cell The influence of trypsin treatment on isolation of the cell was examined. First of all, usual trypsin-EDTA treatment was performed during the stage of isolating and sowing inner cell mass on a feeder cell. As a result, most ES cells were differentiated. When cell aggregate was physically dissociated with a pipette, undifferentiated state could be maintained. It has been clarified that, also in the passage of primary rat ES cell colony, when it is passaged with a trypsin-EDTA treatment, the cells are made to single cells and differentiate, while when it is passaged by dissociating a cell clamp mechanically as mentioned above, the cells can maintain their undifferentiated state.

Figure 5:
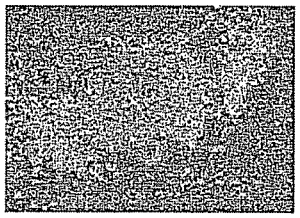
FIG. 5 shows photographs that show the results of comparison of the case rat ES cells are passaged in a state of aggregate consisting of 5-20 cells (a) and the case they are passaged after being completely made to the single cells with trypsin-EDTA solution. A spontaneous differentiation occurs by making them to the single cells.

Then, the influence of trypsin on the 2nd or later passages was examined. That is, difference in the maintenance of undifferentiated state was examined between, at the 2nd passage, when the cells are completely prepared to single cells using trypsin-EDTA and when the cells are passaged as aggregates consisting of 5-20 cells by mechanical operation at the end while minimizing treatment with trypsin-EDTA. As a result, it has been clarified that passage in a single cell state causes spontaneous differentiation, whereas mechanical exfoliation of ES cell colony and passage in an aggregate state consisting of 5-20 cells lead to maintenance of undifferentiated state (FIG. 5).

From the above results, it has been clarified that mouse ES cells are desirably made completely to single cells with a trypsin-EDTA solution, and passaged, but rat ES cells are desirably passaged in an aggregate state consisting of 5-20 cells, following mechanical exfoliation of ES cell colony, because spontaneous differentiation occurs when the method of mouse ES cell is applied to rat ES cells.

5) Establishment of Rat ES Cell

Figure 6:
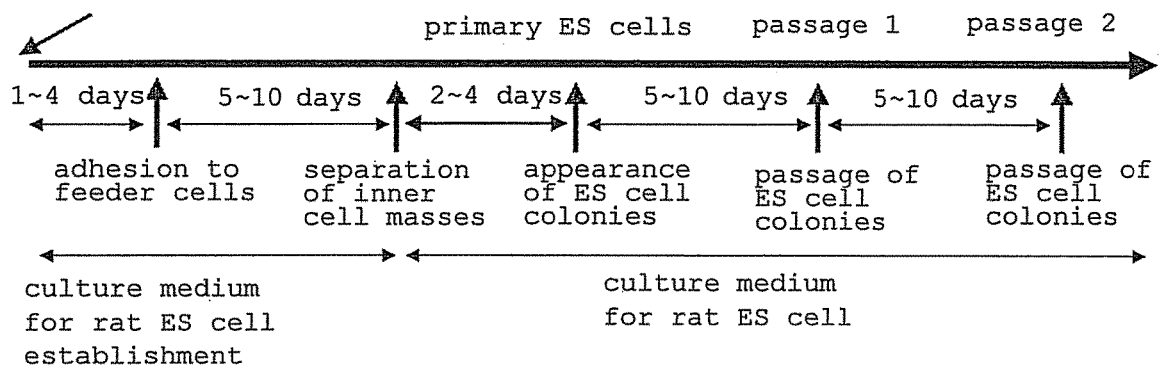
FIG. 6 is a drawing showing the outlines of a method of rat ES cell establishment.

Based on the above examination results, rat ES cell was established. The outline of the establishment method is shown in FIG. 6.

Figure 7:
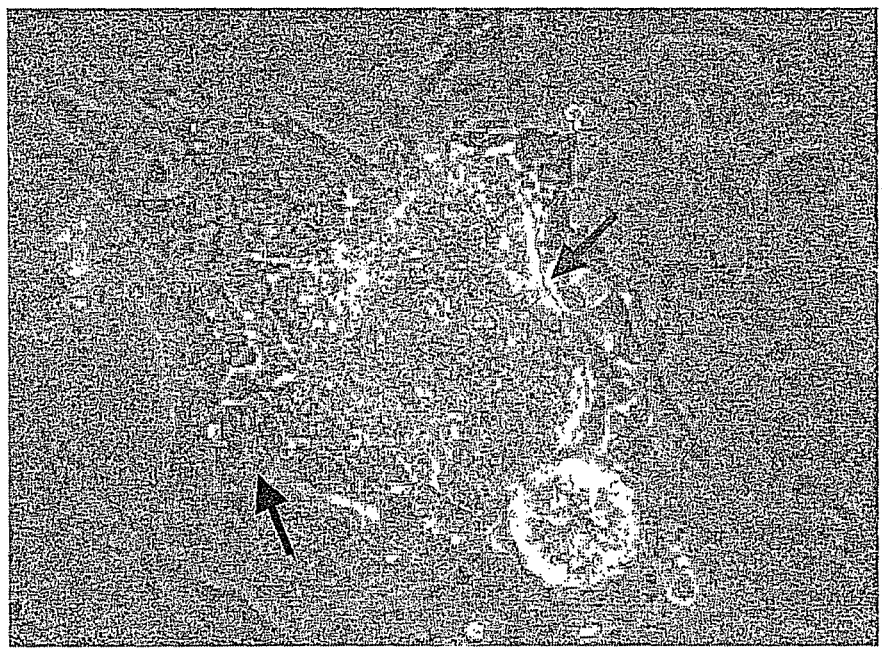
FIG. 7 is a photograph that shows the formation of inner cell masses by culturing zona pellucida-removed rat blastocysts using feeder cells and a culture medium for rat ES cell establishment. The arrows show the inner cell masses formed.
Figure 8:
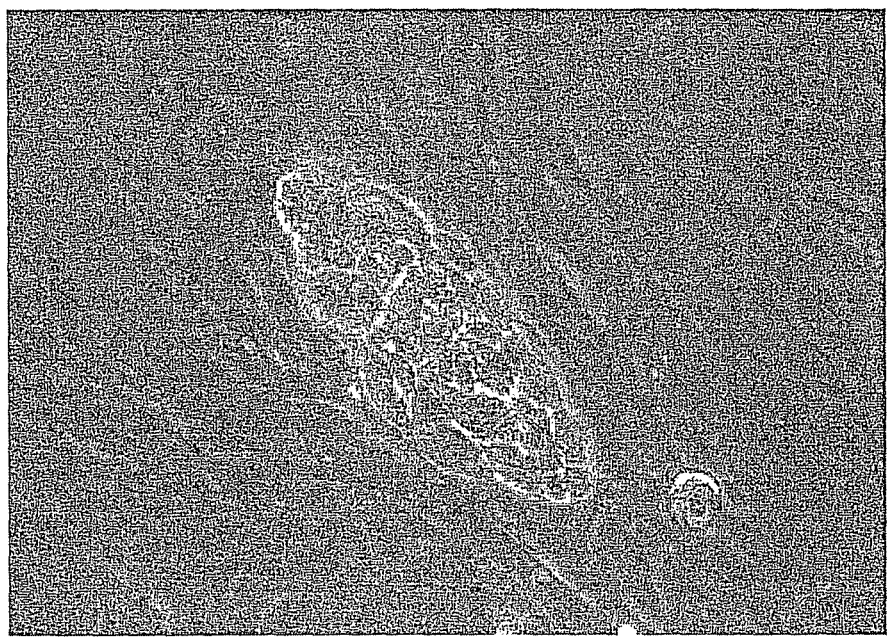
FIG. 8 is a photograph of primary rat ES cells that have appeared by culturing rat inner cell masses using a culture medium for rat ES cells and feeder cells.
Figure 9:
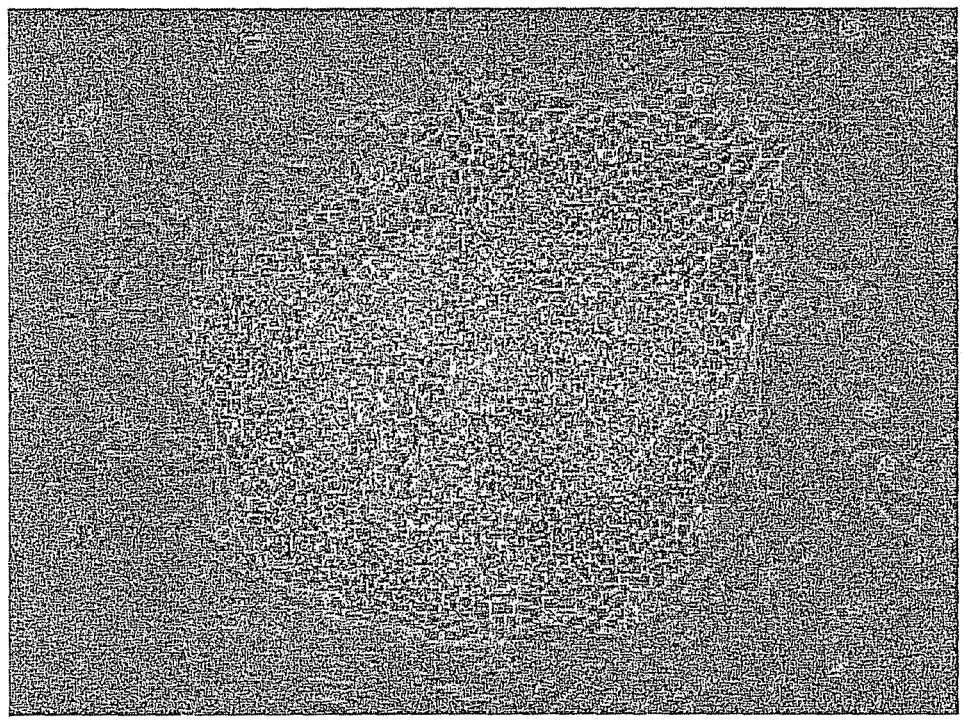
FIG. 9 is a photograph of rat ES cells 7 days after the appearance of the ES cell colonies, which has become the state capable of passage.

After confirmation of rat blastocyst (late stage) under a microscope, zona pellucida was removed using Acidic Tyrode (pH 2.5). Mitomycin C-treated normal mouse embryonic fibroblasts (feeder cells) were sown on a 60 mm gelatin-coated culture dish (Iwaki, Tokyo, Japan), the rat blastocysts (late stage) free of zona pellucida were transferred thereto by 5-10 blastocysts, and cultured in a culture medium for rat ES cell establishment. The rat blastocyst (late stage) without zona pellucida adhered to normal mouse embryonic fibroblasts at day 1-4, the inner cell mass (FIG. 7) alone was separated with a 200 µl pipette at day 5-10 from the adhesion. The culture medium for rat ES cell establishment (200 µl) was dispensed to a 1.5 ml sterile tube, the separated inner cell mass was transferred, and the cell aggregate was mechanically dissociated with a pipette. The dissociated inner cell mass was cultured in a medium for rat ES cell, in a 6-well gelatin-coated culture dish (Iwaki, Tokyo, Japan) containing feeder cells sown thereon the day before use. An ES cell colony appeared in 2-4 days of culture (FIG. 8, and "primary ES cell" in FIG. 6), and an ES cell colony (FIG. 9) at 5-10 days from the appearance of colony was separated with a 200 µl pipette while confirming the morphology under a microscope. In a 6-well gelatin-coated culture dish (Iwaki, Tokyo, Japan) containing feeder cells sown thereon the day before use, the mechanically dissociated ES cell colony was cultured in a culture medium for rat ES cell (in FIG. 6, "passage 1"). An ES cell colony appeared in 2-4 days of culture and passage became possible in 5-10 days.

Figure 10:
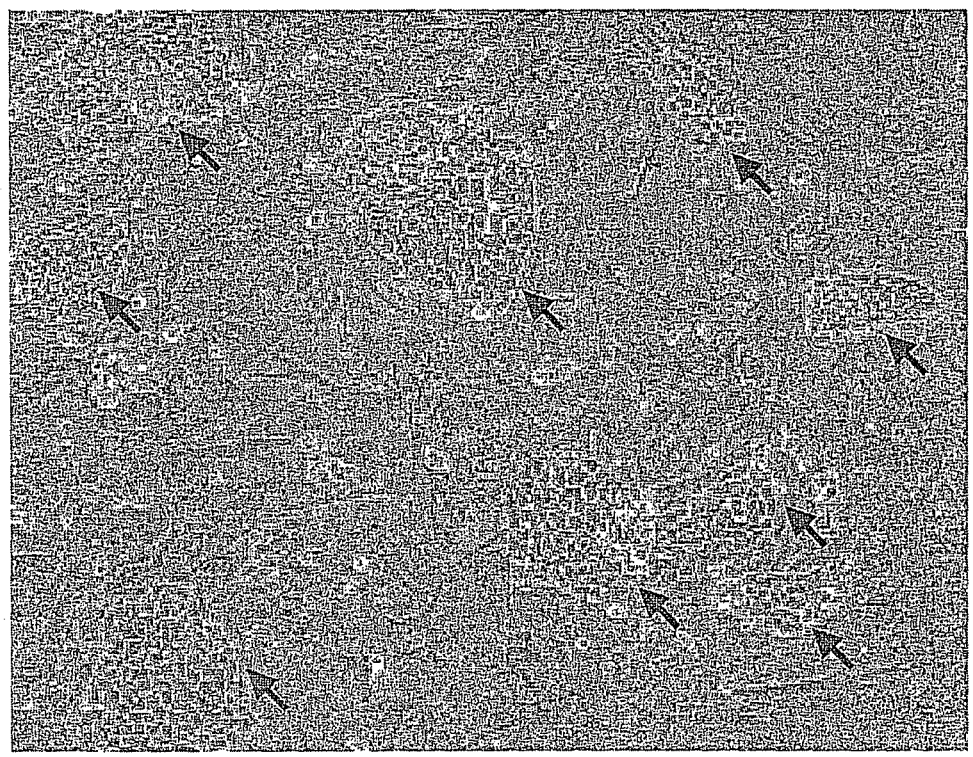
FIG. 10 is a photograph of cell population of rat ES cells (established rat ES cells), which have become capable of stable proliferation and passage by use of a culture medium for rat ES cells and feeder cells.
Figure 11:
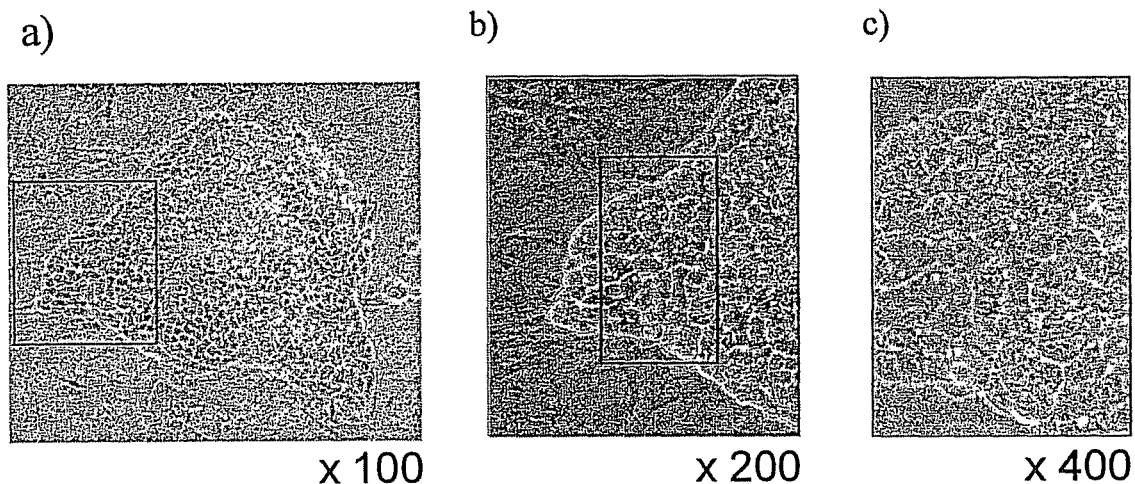
FIG. 11 shows photographs showing the morphology of established rat ES cells. a) is at 100-fold, b) is at 200-fold and c) is at 400-fold magnification.

Then, the culture medium was removed, the cells were washed twice with PBS(−) returned to room temperature, 2.5% trypsin (Gibco BRL, Funakoshi, Tokyo, Japan) incubated at 37° C. in advance was added at 500 µl per 60 mm dish, and the solution was spread over the entire surface and immediately removed. Exfoliation of not less than 70% of ES cell colonies from the feeder cells was confirmed under a microscope and a culture medium (2 ml) containing 10% fetal bovine serum was added to quench the trypsin treatment. Using a 5 ml pipette, the ES cell colonies were further mechanically exfoliated, and the cell suspension was centrifuged (1000 rpm for 3 min, room temperature) to be separated into cells and culture medium, and the cells alone were recovered. The cells were suspended in a culture medium for rat ES cell and, without complete dissociation to single cells, formation of aggregates consisting of 5-20 cells was confirmed under a microscope (FIG. 5, a)), and the cells were cultured in a 60 mm gelatin-coated culture dish (Iwaki, Tokyo, Japan) containing feeder cells sown thereon the day before use (in FIG. 6, "passage 2"). Thereafter, the cells stabilized to a passageable state at day 5-10 were passaged in the same manner as above and the cells at passage 3 or later obtained were taken as established rat ES cells (FIG. 10). The morphology of the established rat ES cell was typical to ES cells and considerably similar to that of various ES cells heretofore reported (FIG. 11). The cells were passaged every 5-10 days in the same manner as above even after the establishment and maintained.

Example 2

Analysis of Established Rat ES Cell

Using rat ES cells of passage 5, the presence of the property as ES cell was confirmed. To be specific, each of the following properties was examined.

1) Analysis of Expression of Marker Gene for Undifferentiated State by RT-PCR Analysis The presence or absence of expression of Oct3/4 and Nanog genes, which are representative markers for undifferentiated state, in the established rat ES cells was confirmed. First of all, total RNA was extracted from the established rat ES cells using ISOGEN (Nippon Gene, Tokyo, Japan). The single strand cDNA was synthesized in a mixture (total amount of 20 µl) including total RNA 2 µg, oligo(dT)$_{18}$ primers 0.5 µl, dNTPs 10 pmol, RAV-2 RTase 5 units, and single strand synthesis buffer (Takara, Kyoto, Japan). Synthesis was performed at 37° C. for 10 min, 42° C. for 1 hr, 56° C. for 10 min, and 99° C. for 5 min In addition, the following primers were synthesized (the oligonucleotide sequences are described in the order of sense, antisense primers in the parenthesis, followed by annealing temperature, cycles for PCR, and length of amplified fragment): β-actin (5'-AGAGCAAGAGAGGTATCCTG-3' (SEQ ID NO:1), 5'-AGAGCATAGCCCTCGTAGAT-3' (SEQ ID NO:2); 55° C.; 25 cycles; 339 bp), Oct 3/4 (5'-ATGGACTACCCAGAACCCCAG-3' (SEQ ID NO:3), 5'-TTACAGGAGCTGCAGTTATAC-3' (SEQ ID NO:4); 56° C.; 35 cycles; 448 bp), Nanog (5'-TAGCCCTGATTCT-TCTAGCA-3' (SEQ ID NO:5), (5'-TTTGCTGCAACG-GCACATAA-3' (SEQ ID NO:6); 54° C.; 35 cycles; 617 bp). The rat Oct 3/4 primers were designed by obtaining a CDS sequence of mouse Oct 3/4 gene from GenBank, searching for its base sequence using BLAST to obtain rat Oct 3/4 gene sequence, searching the homology of mouse and rat, and selecting a region that is not amplified in the case of mouse ES cell, which was used as rat specific Oct 3/4 primers. Primers for Nanog were designed based on the CDS sequences of mouse and human Nanog genes.

Figure 12:
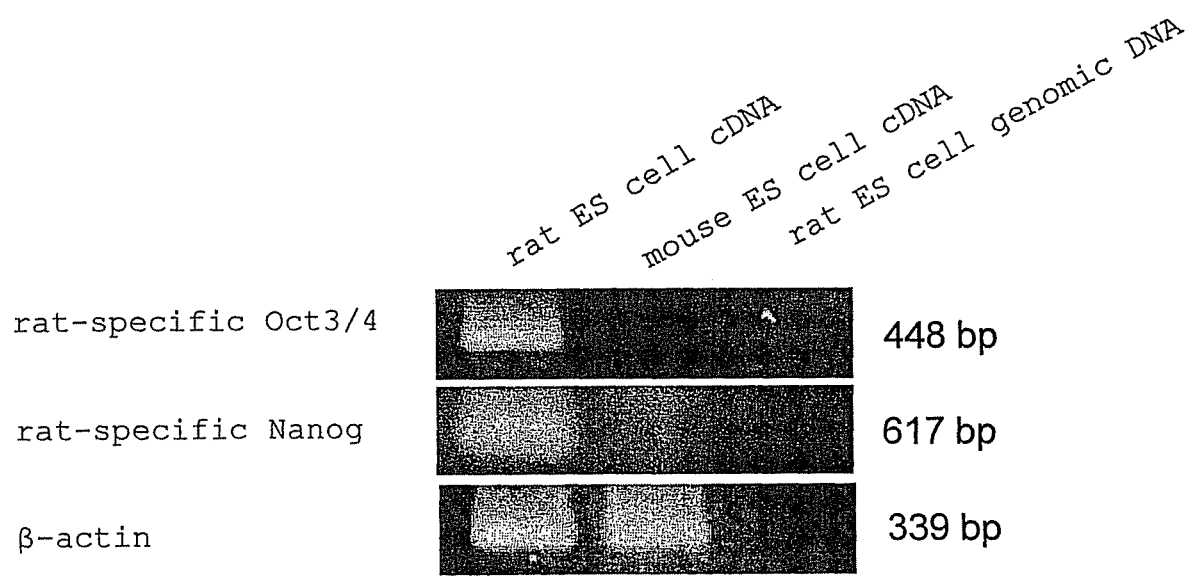
FIG. 12 shows photographs of RT-PCR that demonstrates the expression of marker genes for undifferentiated state in established rat ES cells. The presence or absence of the expression of Oct 3/4 gene and Nanog gene, which are typical marker genes for undifferentiated state in ES cells, were assayed. The expression of $\beta$-actin gene was also analyzed as a control.

Amplification was performed in a mixture (total amount of 50 μl) including template cDNA 4 μl, 100 μM dNTPs, primers 10 pmol, Ex-Taq 1.0 unit and Ex-Taq buffer (Takara, Kyoto, Japan). After PCR, a small amount of the mixture was electrophoresed on a 3.0% agarose gel, stained with ethidium bromide (EtBr), and photographed under UV irradiation. The results are shown in FIG. 12. As is clear from FIG. 12, bands showing amplification of rat specific Oct3/4 and Nanog gene fragments were confirmed only in the cDNA of rat ES cell.

2) Analysis of Alkaline Phosphatase Activity

Figure 13:
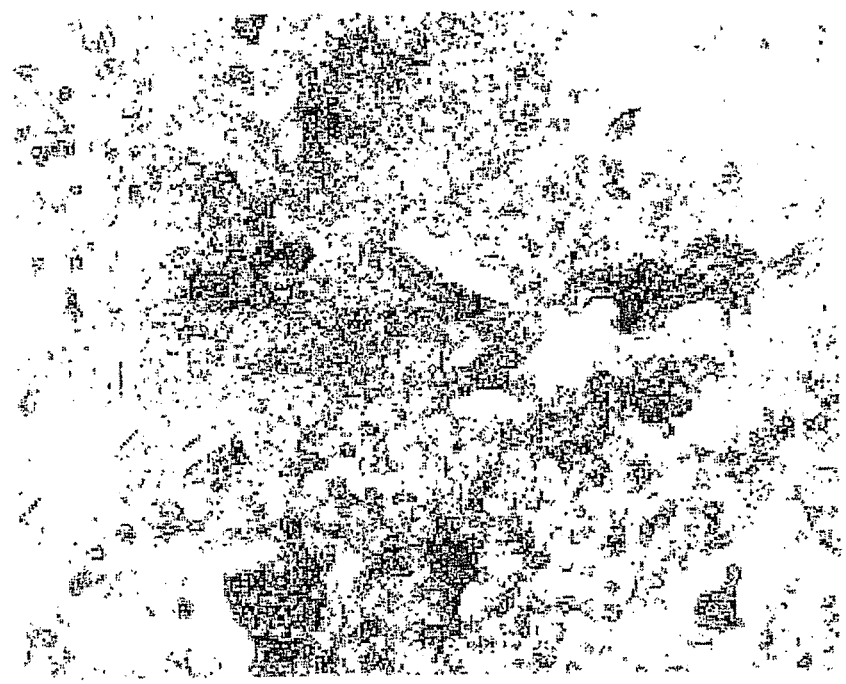
FIG. 13 is a photograph showing an alkaline phosphatase activity of established rat ES cells, which activity is one of the typical indexes demonstrating that they have an ability to keep undifferentiated state.

The presence or absence of alkaline phosphatase activity, which is one of the representative indices verifying that the cell has an undifferentiated state-maintaining ability, was analyzed. First, established rat ES cells cultured in a culture medium for rat ES cell and in the presence of feeder cell were directly fixed with 4% para-formaldehyde for 10 min, and thereafter fixed with 100% EtOH for 10 min. The cells were washed with $H_2O$ for 30 min. The alkaline phosphatase activity was detected with Vector Red Alkaline Phosphatase Substrate Kit I (Funakoshi, Tokyo, Japan) according to the manual. The results are shown in FIG. 13. Established rat ES cell was shown to be alkaline phosphatase activity positive.

3) Analysis of Embryoid Body Forming Ability

Figure 14:
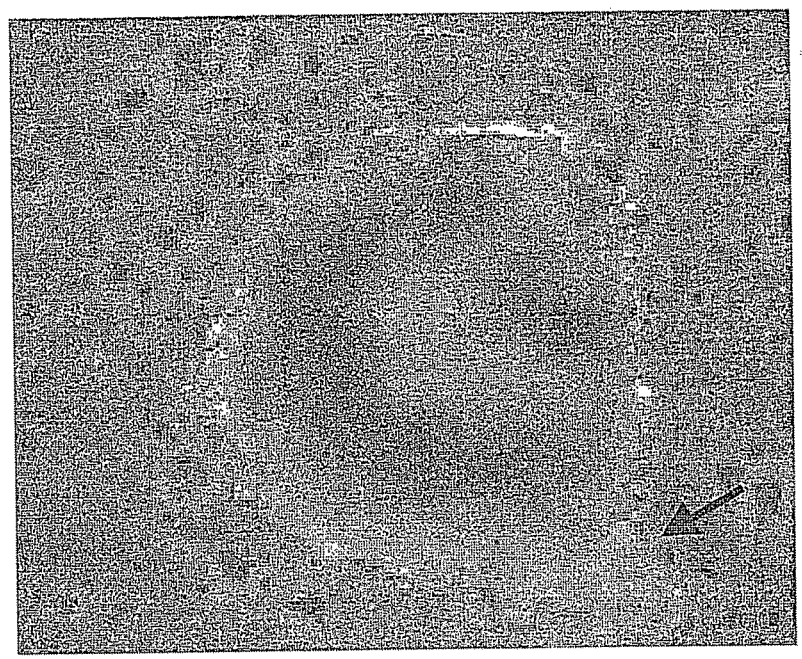
FIG. 14 is a photograph showing the results of the analysis for embryoid body-forming ability of established rat ES cells. About 20 days later, many of embryoid bodies beating like cardiac muscle (arrow) were confirmed.

It is known that embryoid body is formed by culturing ES cells under the conditions free of feeder cell and LIF in a non-coated culture dish (Roy, S. et al., *Mol. Cell. Biol.*, 18: 3947-3955 (1998)). Thus, established rat ES cells ($1.0 \times 10^7$ cells) were sown on an rLIF-free culture medium for rat ES cell in a non-coated culture dish, and incubated at 37° C. for 20 days while exchanging the culture medium every 3 days. The results are shown in FIG. 14. As is clear from FIG. 14, the embryoid body was formed, and many embryoid bodies showing cardiac muscle-like beating were confirmed.

4) ES Cell Marker Staining Analysis

Figure 15:
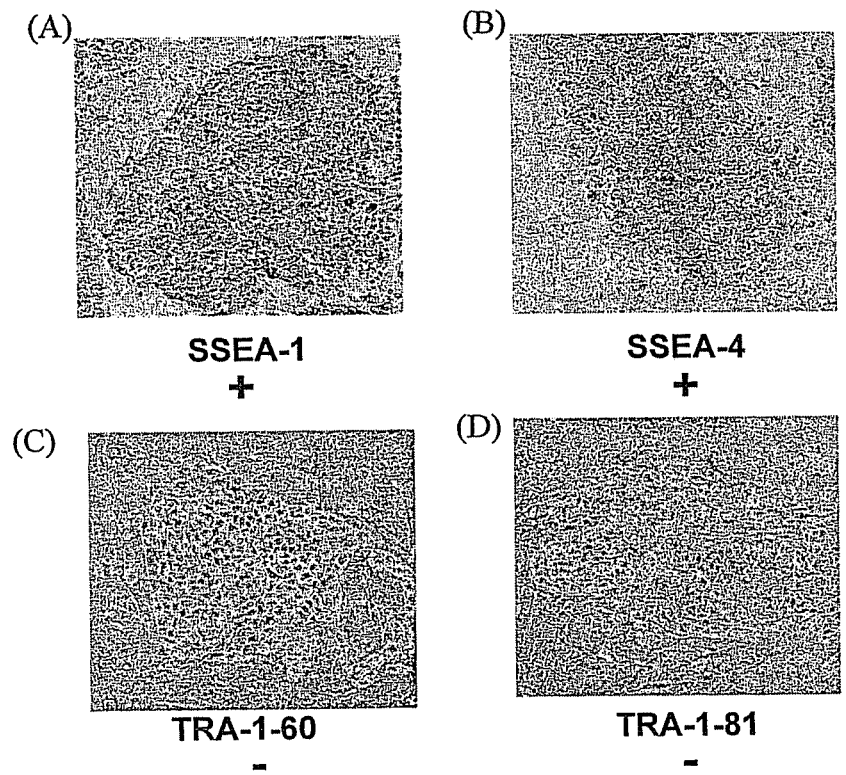
FIG. 15 show photographs presenting the results of immunostaining using 4 kinds of marker antibodies ((A): SSEA-1, (B): SSEA-4, (C): TRA-1-60, (D): TRA-1-81) which give an indication that the established cells are ES cells.

The presence or absence of the expression of markers for undifferentiated state was examined. Established rat ES cells cultured in a culture medium for rat ES cell and in the presence of feeder cell were directly fixed with 4% para-formaldehyde for 10 min and thereafter stood in 0.02% Triton X-100 for 15 min, and stood in 3% aqueous hydrogen peroxide/methanol for 15 min. After blocking with 5% serum/PBS for 15 min, SSEA (stage-specific embryonic antigen)-1, SSEA-4, TRA-1-60 and TRA-1-81, each of which is a representative membrane protein of ES cell and one kind of marker for undifferentiated state, were detected with ES cell Characterization Kit (Funakoshi, Tokyo, Japan) and a secondary antibody (anti-mouse IgG antibody-biotinylated (Funakoshi, Tokyo, Japan)), and a DAB staining kit (Kowa, Tokyo, Japan), according to the manual. The results are shown in FIG. 15. SSEA-1 and SSEA-4 were positive and expression of these markers for undifferentiated state was shown. As for TRA-1-60 and TRA-1-81, expression could not be detected from the antibody staining results.

5) Analysis of Chromosome Number

Figure 16:
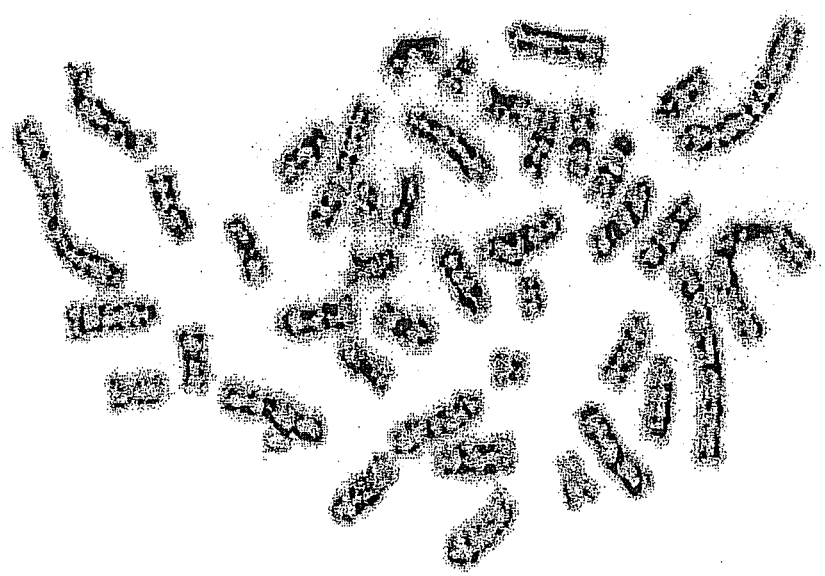
FIG. 16 is a photograph showing the analysis of the chromosome number of the established rat ES cell using G-banding method, which indicates the same chromosome number (2n=42) as that of normal rat cell.

Whether or not the established rat ES cell maintains the normal chromosome number was confirmed. The established rat ES cells were cultured in a culture medium for rat ES cell in a feeder cell-free gelatin-coated culture dish (Iwaki, Tokyo, Japan), and the chromosome number was analyzed by the G-banding method (Sumner, A. T. *Cancer Genet. Cytogenet.* 6: 59-87 (1982)). The results are shown in FIG. 16. The normal chromosome number (2n=42) of rat cells was shown to have been maintained.

6) Analysis of Number of Passages

Figure 17:
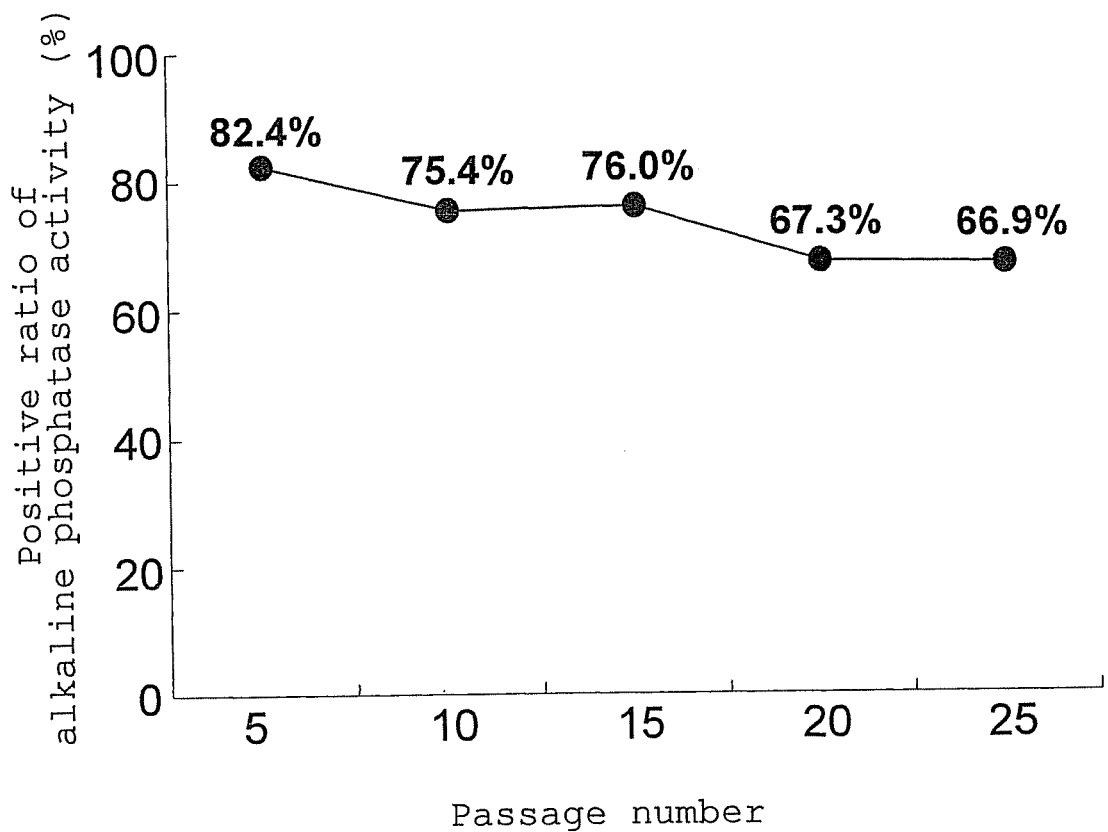
FIG. 17 is a graph showing the relationship between the passage number of established rat ES cells and their ability to keep undifferentiated state (alkaline phosphatase activity). The staining for alkaline phosphatase activity was started at passage 5, and then performed after every 5 passages. The vertical axis shows the number of positive ES cell colonies divided by the number of total ES cell colonies in percentage. The horizontal axis shows the passage number.

The number of passages and undifferentiated state-maintaining ability maintenance rate of the established rat ES cell were examined. Rat ES cells were cultured in a culture medium for rat ES cell in a feeder cell-free gelatin-coated culture dish (Iwaki, Tokyo, Japan), and the number of passages and maintenance of undifferentiated state-maintaining ability were examined with alkaline phosphatase activity as an index. The test was started with passage 5, and alkaline phosphatase activity staining was conducted every 5 passages. The alkaline phosphatase activity was detected using a Vector Red Alkaline Phosphatase Substrate Kit I (Funakoshi, Tokyo, Japan) according to the manual. The results are shown in FIG. 17. It has been clarified that the rat ES cells can be cultured by the use of a culture medium for rat ES cell until at least passage 25, while maintaining a stable undifferentiated state-maintaining ability. It has been clarified that stable culture is possible thereafter until passage 35.

7) Analysis of In Vitro Pluripotency

The spontaneous differentiation ability of the established rat ES cell was examined. Established rat ES cells ($1.0 \times 10^7$ cells) were cultured in a culture medium for rat ES cell free of a rat leukemia inhibitory factor (rLIF) in a non-coated culture dish (Iwaki, Tokyo, Japan) to initiate embryoid body formation. On day 7 from the start of the formation, the embryoid body was transferred to a gelatin-coated culture dish (Iwaki, Tokyo, Japan) and further cultured for 7 days. The results are shown in FIG. 18.

Figure 18:
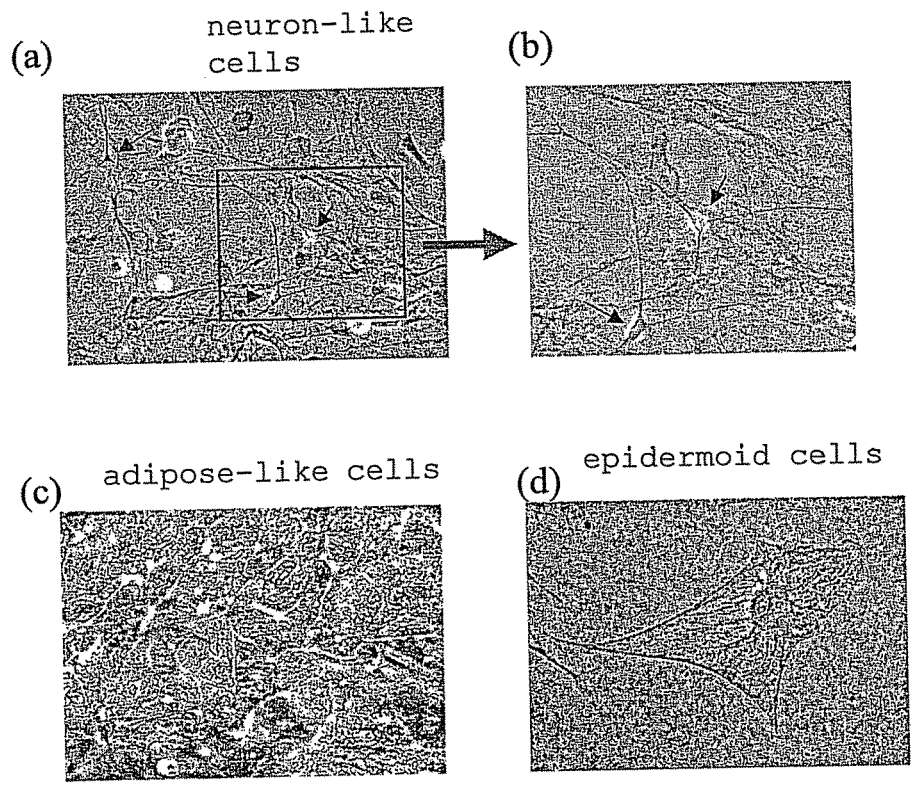
FIG. 18 shows photographs demonstrating that established rat ES cells have a pluripotency in in vitro system. Seven days after initiation of embryoid body formation, the embryoid bodies were transferred to a gelatin-coated culture dish to induce a spontaneous differentiation. (a) a photograph of rat ES cell-derived neuron-like cells, (b) a close-up picture of the area surrounded by square in Fig. (a), (c) a photograph of rat ES cell-derived adipose-like cells, (d) a photograph of rat ES cell-derived epidermoid cells.

As shown in FIG. 18(*a*), neuron-like cells emerged from the embryoid body. In the enlarged view (b) of the neuron-like cells, an image wherein neurite is extended between two cells to connect them is confirmed. While the adipose-like cell is characterized in that it contains many clear granules in the cytosol, as shown in FIG. 18(*c*), an adipose-like cell image containing many clear granules was confirmed. As shown in FIG. 18(*d*), many epithelium-lineage cells were also confirmed. As evidenced, it has been confirmed that the established rat ES cell has an ability to spontaneously differentiate to various cells.

8) Influences of Serum and LIF Addition on Rat ES Cell

Influences of LIF and serum on the established rat ES cell in the maintenance of the undifferentiated state-maintaining ability and growth ability were examined. Rat ES cell (passage 5) were subcultured for one generation under the following 4 kinds of culture conditions. (1) containing rat LIF (rLIF), serum-free (containing 20% KSR), (2) without LIF, serum-free (containing 20% KSR), (3) containing mouse LIF (mLIF), serum-free (containing 20% KSR), and (4) containing rat LIF (rLIF), containing 20% serum.

Whether or not the undifferentiated state-maintaining ability was maintained was examined by analyzing the presence or absence of expression of each gene of Oct3/4, Nanog and Rex-1, which are undifferentiated state-marker genes of ES cell. In addition, the presence or absence of expression of ERas gene, which is important for teratoma formation characteristic of ES cells was also analyzed. The sequence of the primers used, annealing temperature and cycles of PCR are as shown below.

Oct 3/4:

(SEQ ID NO: 3)
5'-ATGGACTACCCAGAACCCCAG-3',

-continued

```
                                           (SEQ ID NO: 4)
5'-TTACAGGAGCTGCAGTTATAC-3', 56° C., 40 cycles, Nanog:
                                           (SEQ ID NO: 5)
5'-TAGCCCTGATTCTTCTAGCA-3', (SEQ ID NO: 6)
5'-TTTGCTGCAACGGCACATAA-3' 60° C., 40 cycles, Rex-1:
                                           (SEQ ID NO: 7)
5'-AAATCATGACGAGGCAAGGC-3'

(SEQ ID NO: 8)
5'-TGAGTTCGCTCCAACAGTCT-3' 60° C., 40 cycles,

ERas:
                                           (SEQ ID NO: 9)
5'-ACCTGAGCCCCGGCACACAG-3'

(SEQ ID NO: 10)
5'-CAGCTGCAGCGGTGTGGGCG-3' 64° C., 40 cycles.
```

Figure 19:
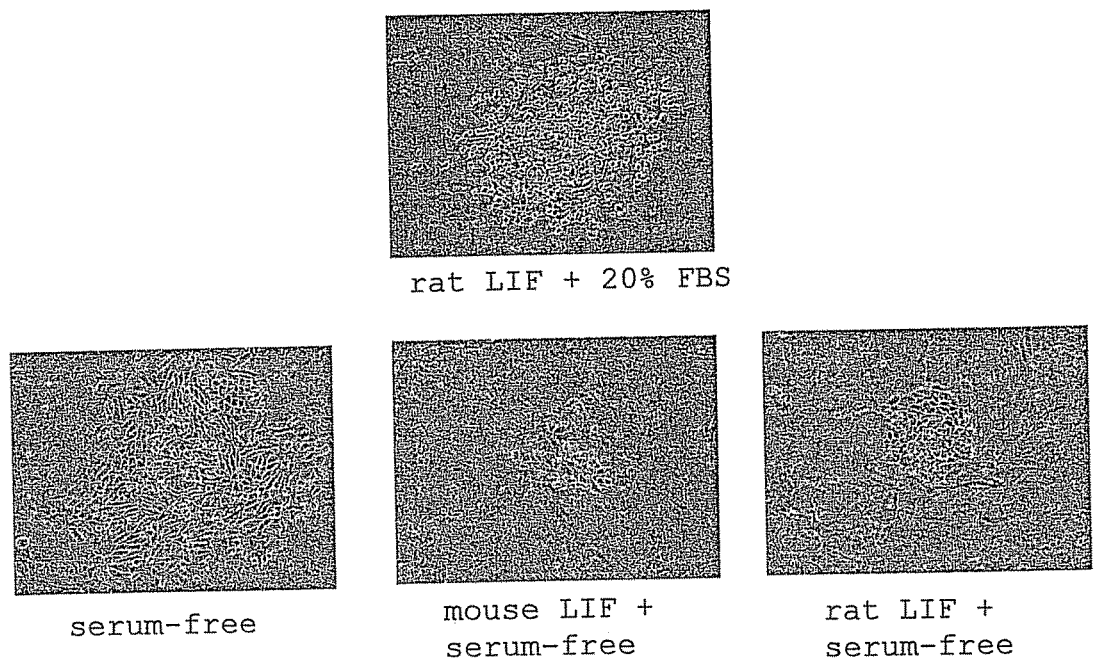
FIG. 19 shows photographs showing the results of study on the effects of serum/LIF addition on established rat ES cells. In the figure, "rat LIF+20% FBS" shows the result of the culture under the conditions containing rat LIF (rLIF) and 20% serum, "serum-free" shows the result of the culture under the conditions free of LIF and serum (containing 20% KSR), "mouse LIF+serum-free" shows the result of the culture under the conditions containing mouse LIF (mLIF) and free of serum (containing 20% KSR), and "rat LIF+serum-free" shows the result of the culture under the conditions containing rat LIF (rLIF) and serum free (containing 20% KSR), respectively.

Furthermore, a morphological observation was also performed. The results are shown in FIG. 19.

When rat ES cells were cultured using rLIF and 20% KSR (the aforementioned (1)), they were morphologically stable (FIG. 19), and expression of the ES cell marker genes was observed. Thus, it has been confirmed that cell growth is possible while maintaining the undifferentiated state-maintaining ability. On the other hand, when cultivated under the other 3 conditions (the aforementioned (2)-(4)), expression of characteristic ES cell markers disappeared, and a shift to a morphologically differentiated state was observed (FIG. 19). From the above results, it has been clarified that that both rat LIF and serum replacement reagent (KSR) are important for the culture of rat ES cells.

9) Analysis of Teratoma Forming Ability

Established rat ES cells are adjusted to $1.0 \times 10^7$ cells/200 μl with PBS to give a suspension, and subjected to cell transplantation to the inside of the testis and the subdermic of syngeneic male rat (15-week-old). The rat is sacrificed, and the formed teratoma is excised and fixed with 4% para-formaldehyde. A tissue section is prepared, stained with hematoxylin/eosin, and differentiation induction to three embryonic germs (endoderm, mesoderm and ectoderm) is confirmed under a microscope.

10) Analysis of Chimeric Rat-Producing Ability

A chicken albumin promoter is incorporated into a pEGFP-1 vector (clonetech) at the upstream of EGFP gene and constructed as a vector permitting stable intracellular expression of EGFP gene. The prepared vector was introduced into the rat ES cell by the electroporation method, a cell line (RESC/EGFP strain), in which the vector has been incorporated into the chromosomal gene in the rat ES cell was established by selection using a drug G418.

Separately, an ES cell-syngeneic rat was naturally crossbred and, on day 3 after confirmation of vaginal plug, the female rat for oocyte sampling was sacrificed. The uterus was excised, perfused with MW medium and oocytes were recovered. Thereafter, 40 sampled oocytes are developed in a 5% $CO_2$ incubator up to 8-cell embryo. Zona pellucida is removed in an oil drop using Acidic Tyrode (pH 2.5), the feeder cell is removed, one cell aggregate (5 to 20 cells) of the rat ES cell line (RESC/EGFP cells) established above is introduced into the fertilized oocyte of the syngeneic rat by the microinjection method. The oocyte for transplantation is cultured overnight in a 5% $CO_2$ culture apparatus. Separately, a previously vasoligated male rat and a female rat for oocyte sampling are crossed, vaginal plug of the female rat is confirmed the next day to give a pseudopregnant female rat. The anesthetized pseudopregnant female rat is opened, and 10 oocytes for transplantation are placed in the uterus. The offspring is removed by natural childbirth or caesarotomy when particularly needed, the offspring rat is exposed to fluorescence irradiation and the birth of a chimeric rat is confirmed by the fluorescent body color.

Example 3

Establishment of ES Cell and Analysis of Established Rat ES Cell (2)

1) Establishment of ES Cell

Figure 20:
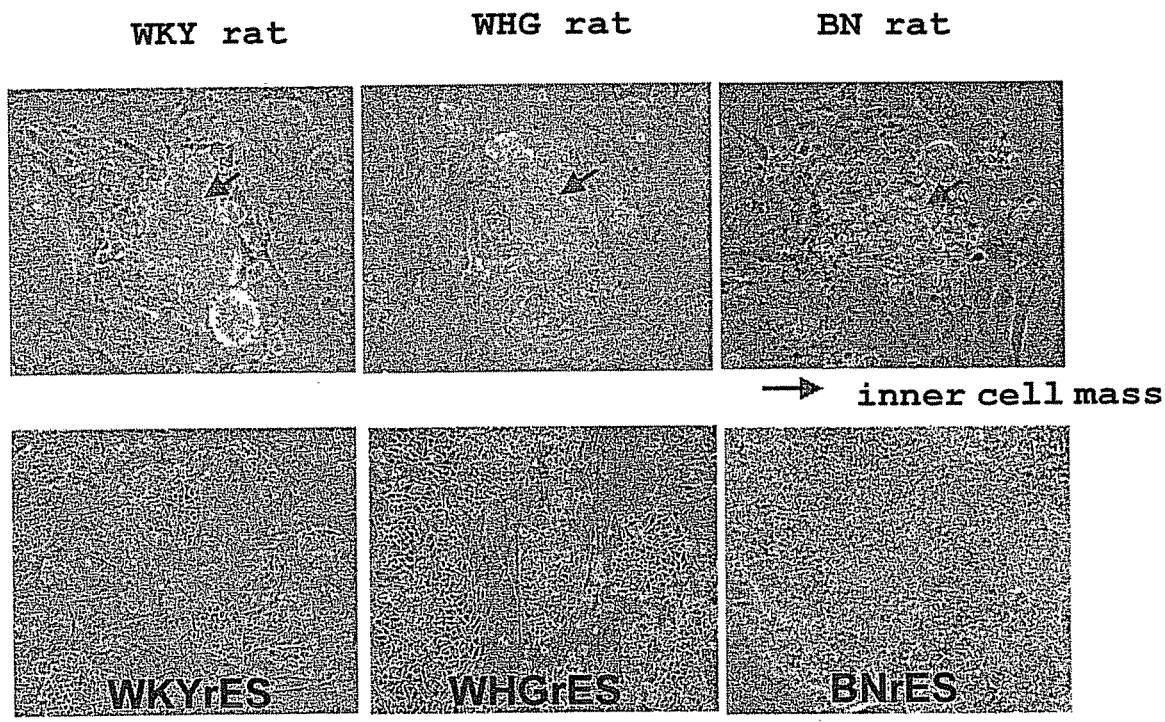
FIG. 20 shows photographs showing the results that ES cells were established form each rat (WKY, WHG and BN). Upper figure: photographs of inner cell masses formed from each rat blastocysts. In the figure, the arrows show inner cell masses formed. Lower figure: photographs of established ES cells at passage 5. In the figure, WKYrES shows ES cells established from WKY rat, WHGrES shows ES cells established from WHG rat and BNrES shows ES cells established from BN rat, respectively.

In the same manner as in the case of Wistar Kyoto rat (WKY) shown in Example 1, ES cell was also established in Wistar Hannover GALAS rat (WHG) and Brown Norway rat (BN). As a result, ES cells of both rats could be established. The photographs of the inner cell masses formed from the blastocysts of respective rats (WKY, WHG and BN) are shown in FIG. 20. The photographs of the established ES cells (passage 5) are also shown in FIG. 20. It was confirmed that, in both the WHG rat ES cell and BN rat ES cell, subculture while holding the undifferentiated state-maintaining ability as in WKY rat ES cell was possible.

2) Analysis of Expression of ES Cell Marker Genes by RT-PCR Analysis

Figure 21:
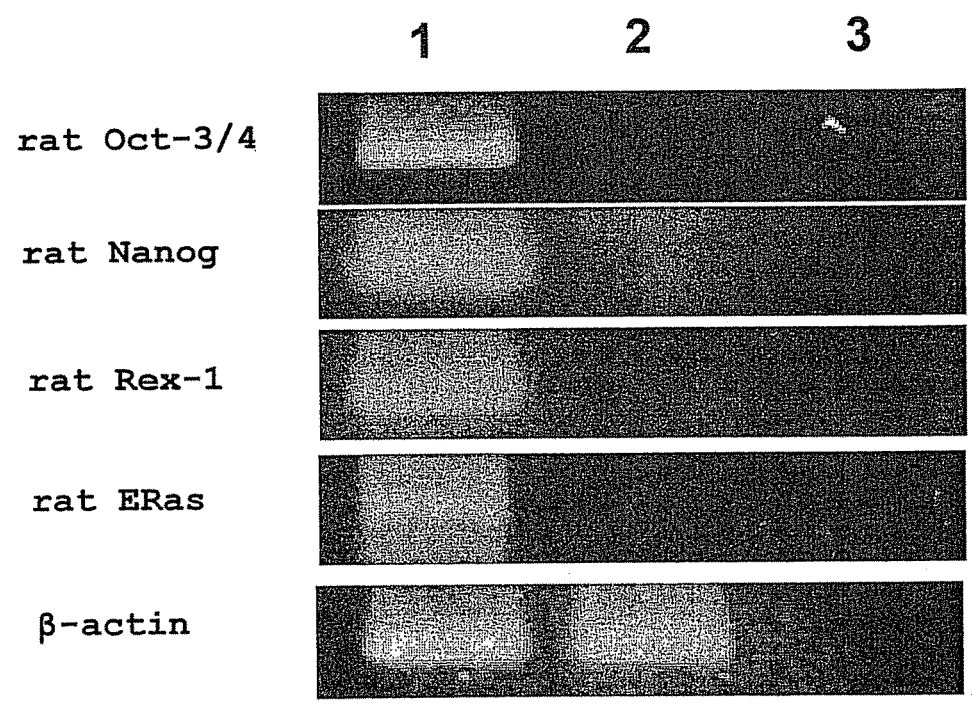
FIG. 21 shows photographs of RT-PCR demonstrating that the established rat ES cells (WKY rat ES cells) express ES cell-marker genes. The gene expression of each factor of typical marker genes for ES cells, Oct3/4, Rex-1, Nanog and ERas was analyzed. The expression of $\beta$-actin gene was also analyzed as a control. Lane 1: undifferentiated rat ES cells, Lane 2: mouse fibroblasts, Lane 3: no template DNA (control). RNA was extracted from each samples and RT-PCR was performed.

The presence or absence of the expression of ES cell marker genes in the established WKY rat ES cell, WHG rat ES cell and BN rat ES cell was confirmed by RT-PCR analysis. The experiment was performed in the same manner as in Example 2, 1). Expression of Oct3/4, Rex-1 and Nanog genes, which are undifferentiated state-marker genes of ES cell was analyzed. Expression of ERas gene important for teratoma formation characteristic of ES cell was also analyzed. As the primers for RT-PCR, those shown in Example 2, 1) and 8) were used. The results of WKY rat ES cell are shown in FIG. 21. Expression was observed for all factors of Oct3/4, Rex-1, Nanog and ERas. The same results were obtained for WHG rat ES cell and BN rat ES cell.

3) Analysis of Embryoid Body Formed from ES Cell

Established rat ES cells were sown in a culture medium for rat ES cell free of rLIF in a non-coated culture dish, and the cells were incubated at 37° C. for 20 days, during which the culture medium was exchanged every 3 days. As a result, an embryoid body was formed, and many embryoid bodies showing beating like cardiac muscle were confirmed.

Then, RNA was extracted from the embryoid body having cardiomyocyte-like cells, and expression of each marker gene of neuron (ectoderm), cardiomyocyte (mesoderm) and hepatocyte (endoderm) was analyzed by RT-PCR. The name of each marker gene, primer sequences, annealing temperature and cycles of PCR are as shown below.

```
A) neuron marker
Nestin:
                                          (SEQ ID NO: 11)
5'-GCTCTGACCTATCATCTGAG-3', (SEQ ID NO: 12)
5'-AGATGCACAGGAGATGCTAC-3', 58° C., 40 cycles, TUJI:
                                          (SEQ ID NO: 13)
5'-GGAACGCATCAGTGTCTACT-3',
```

-continued

```
                                    (SEQ ID NO: 14)
5'-ACCACGCTGAAGGTGTTCAT-3'  60° C., 40 cycles, MSI-1:
                                    (SEQ ID NO: 15)
5'-TCTCACTGCTTATGGTCCGA-3', (SEQ ID NO: 16)
5'-TCAGTGGTACCCATTGGTGA-3', 60° C., 40 cycles, GFAP:
                                    (SEQ ID NO: 17)
5'-GGCTCTGAGAGAGATTCGCA-3', (SEQ ID NO: 18)
5'-ATGTCCAGGGCTAGCTTAAC-3', 58° C., 40 cycles, B) cardiomyocyte marker
CCC:
                                    (SEQ ID NO: 19)
5'-TCTGAAGCGGCAGAAGAATC-3'

(SEQ ID NO: 20)
5'-TGACCTCGATGAACTTGGGA-3'  58° C., 40 cycles,

ANF:
                                    (SEQ ID NO: 21)
5'-ATACAGTGCGGTGTCCAACA-3'

(SEQ ID NO: 22)
5'-TTATCTTCGGTACCGGAAGC-3'  58° C., 40 cycles,

KvLQT1:
                                    (SEQ ID NO: 23)
5'-TGCGGATGCTGCATGTTGAT-3'

(SEQ ID NO: 24)
5'-CAAACCCAGAGCCAAGTATG-3', 58° C., 40 cycles,

C) hepatocyte marker
ALB:
                                    (SEQ ID NO: 25)
5'-GCTTGCTGTGATAAGCCAGT-3', (SEQ ID NO: 26)
5'-TGGCAGACAGATAGTCTTCC-3'  58° C., 40 cycles, TDO:
                                    (SEQ ID NO: 27)
5'-CGATGAGAAGCGTCATGACT-3', (SEQ ID NO: 28)
5'-AACCAGGTACGATGAGAGGT-3', 58° C., 40 cycles, TAT:
                                    (SEQ ID NO: 29)
5'-AATGAGATTCGAGACGGGCT-3', (SEQ ID NO: 30)
5'-TTCATCACAGTGGTAGTGCT-3', 58° C., 40 cycles, G6P:
                                    (SEQ ID NO: 31)
5'-GTCAACGTATGGATTCCGGT-3', (SEQ ID NO: 32)
5'-GTTCTCCTTTGCAGCTCTTG-3'  58° C., 40 cycles.
```

Figure 22:
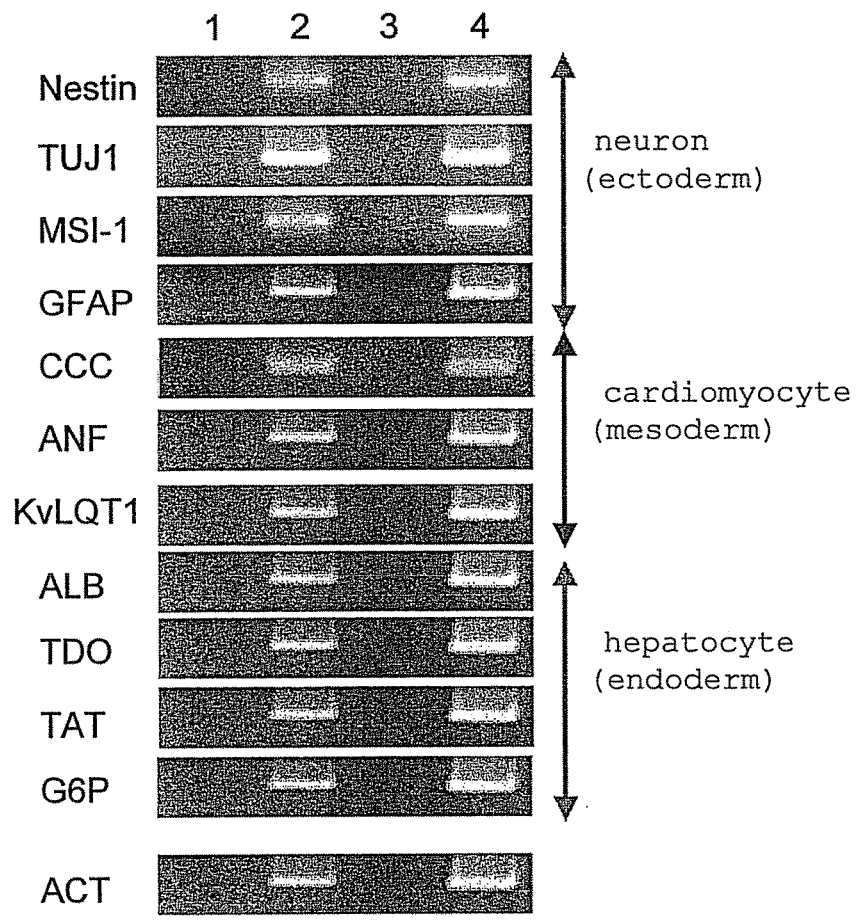
FIG. 22 shows photographs of RT-PCR demonstrating that embryoid bodies formed from established rat ES cells (WHG rat ES cells) differentiate to cells of three embryonic germ lineages. In the figure, the name of each maker gene is shown in the left side: TUJ1 shows beta3-tublin, MSI-1 shows musashi-1, GFAP shows glial fibrillary acidic proteins alpha, CCC shows cardiac dihydropyridine-sensitive calcium channel protein, ANF shows atrial natriuretic factor, ALB shows albumin, TDO shows tryptophan 2,3-dioxygenase, TAT shows tyrosine aminotransferase, G6P shows glucose-6-phospatase and ACT shows β-actin, respectively. Lane 1: undifferentiated rat ES cells, Lane 2: rat ES cell-derived embryoid bodies, Lane 3: control (no template DNA), Lane 4: each organ derived from a WHG individual (brain, heart, liver). RNA was extracted from each samples and RT-PCR was performed.

The results of RT-PCR are shown in FIG. 22. It has been clarified that genes free of expression in an undifferentiated state (lane 1) all turned positive in the embryonic body (lane 2). From the results, it has been clarified that established rat ES cells have an ability to differentiate to the cells of three embryonic germ (ectoderm, mesoderm, endoderm) lineages, namely, they have the properties of ES cell.

4) Analysis of Teratoma Formation Ability

Figure 23:
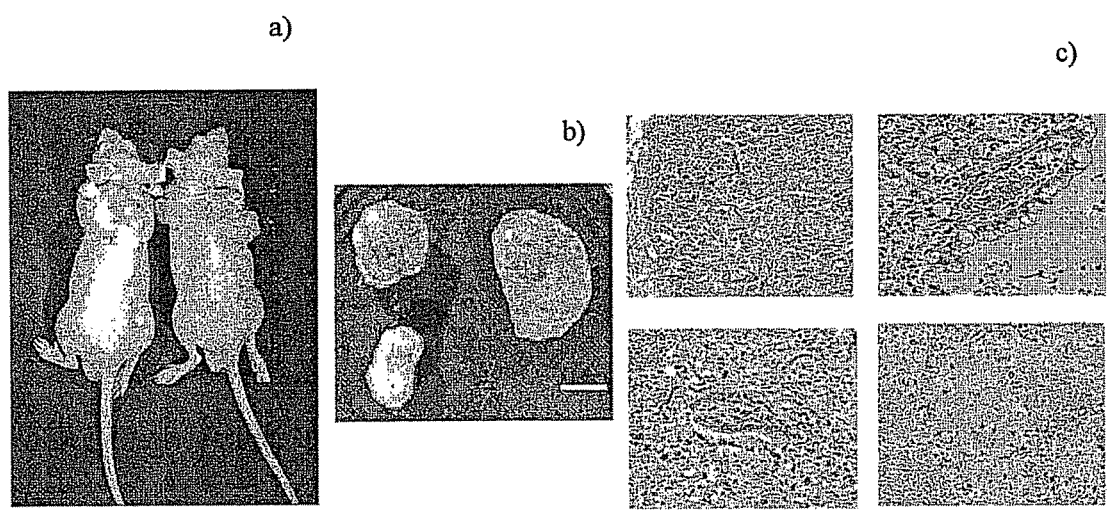
FIG. 23 shows photographs demonstrating that teratomas were formed by subcutaneously implanting the established rat ES cells (WHG rat ES cells) to mice, and that the teratomas have three embryonic germ lineage structures. a): a photograph of mice in which teratomas were formed by subcutaneously implanting WHG rat ES cells to immunodeficient mice. The lumps at the necks are teratomas. b): a photograph of the dissected teratomas. In the figure, the size bar shows 1 cm. c): histologies of a teratoma sectioned and stained with hematoxylin/eosin. The upper left shows gland structure, the upper right shows vascular endothelium-like structure, the lower left shows intestinal tract-like structure and the lower right shows osteocyte-like structure, respectively.

The established WKY rat ES cell, WHG rat ES cell, and BN rat ES cell ($2.5 \times 10^7$ cells) were each subcutaneously transplanted to immunodeficient mice. One or two months later, formation of teratoma was confirmed in all of these ES cell-transplanted mice. The results of WHG rat ES cell are shown in FIG. 23. The mice were sacrificed, formed teratoma was excised and fixed with 4% para-formaldehyde. Tissue sections were prepared and stained with hematoxylin/eosin (FIG. 23). By observation under a microscope, respective tissues of glandular structure (mesoderm lineage), blood vessel endotheloid structure (ectoderm lineage), intestine-like structure (endoderm lineage), and osteocyte-like structure (mesoderm lineage) were observed. From the above results, it has been clarified that the established rat ES cells have a teratoma-forming ability, and the formed teratomas have three embryonic germ (endoderm, mesoderm and ectoderm) structures.

5) Analysis of Chimeric Rat-Producing Ability pCAG-EGFP gene was introduced into a rat ES cell (WHG rat ES cell) by the electroporation method to prepare a WHG rat ES cell line (hereinafter to be abbreviated as pCAG-EGFP/WHGrES cell line) in which pCAG-EGFP gene is integrated into a chromosome.

A female rat syngeneic with WHG rat ES cell was naturally crossbred and, after confirmation of the presence of vaginal plug the next day, oocytes were sampled on day 4. Thereafter, fertilized oocytes developed to the blastocyst stage in a 5% $CO_2$ incubator were harvested, and 8-12 pCAG-EGFP/WHGr ES cells were transplanted per 1 oocyte by the microinjection method (hereinafter to be abbreviated as ES(+)).

Separately, a vasoligated syngeneic male rat and a syngeneic female rat were crossed and the presence of vaginal plug was confirmed the next day, to prepare a pseudopregnant female rat. On day 4 of confirmation of the presence of vaginal plug, 6-10 ES(+)oocytes were transplanted per 1 pseudopregnant rat. Thereafter, the offspring rat (GFP chimeric rat) was excised by caesarotomy.

Figure 24:
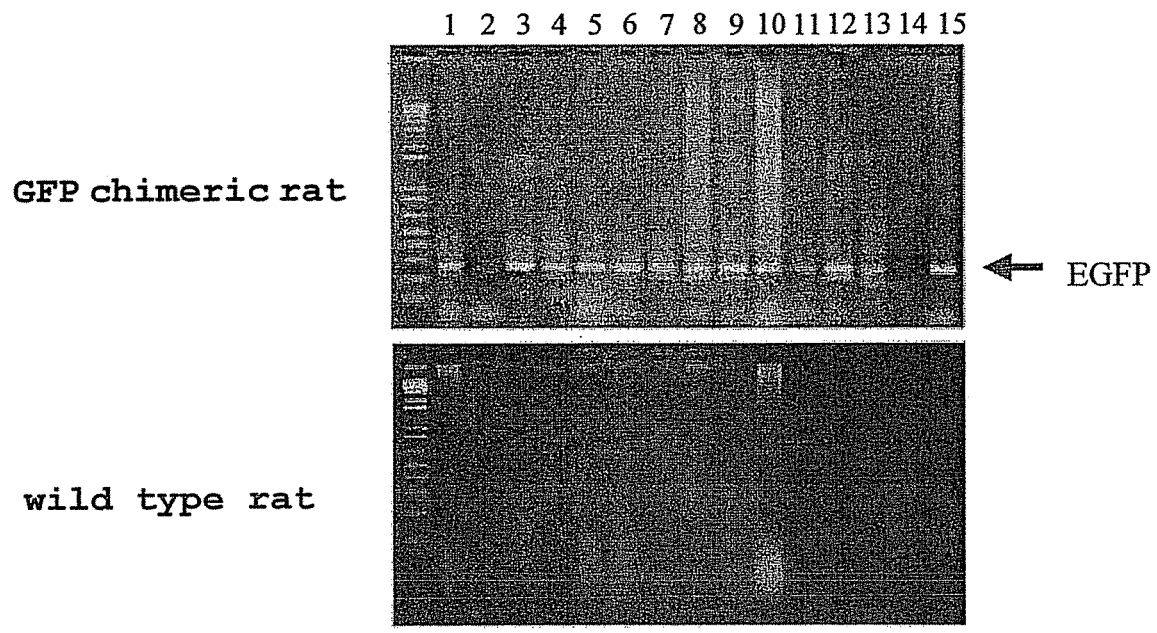
FIG. 24 shows photographs of genomic PCR demonstrating that EGFP is expressed in almost tissues in a chimeric rat produced using established gene-introduced rat ES cells (pCAG-EGFP/WHGrES cells). The upper figure shows the results in the chimeric rat produced using pCAG-EGFP/WHGrES cells, the lower figure shows the results in a wild-type rat. Lane 1: brain, Lane 2: thymus, Lane 3: heart, Lane 4: esophagus, Lane 5: lung, Lane 6: stomach, Lane 7:pancreas, Lane 8: small intestine, Lane 9: large intestine, Lane 10: liver, Lane 11: spleen, Lane 12: kidney, Lane 13: testis, Lane 14: blood vessel, Lane 15: muscle. Chromosome DNA was extracted from each tissue, and genomic PCR was performed.

Various tissues were separated from the GFP chimeric rat, and genomic DNA was extracted. Using the genomic DNA as a template and GFP specific primers, genomic PCR was performed according to a conventional method. The results are shown in FIG. 24. As a result, a band corresponding to GFP gene suggesting pCAG-EGFP/WHGrES cell derivation was confirmed in all organs examined except 3 organs (thymus, blood vessel, spleen). In contrast, a band corresponding to GFP gene was not confirmed in the control (wild-type rat) genome. It has been clarified that the established rat ES cell has a chimeric rat-producing ability, since, as shown above, a gene derived from rat ES cell (pCAG-EGFP/WHGrES cell) was contained in each tissue or cell.

6) Analysis of Chimeric Rat Tissue

Figure 25:
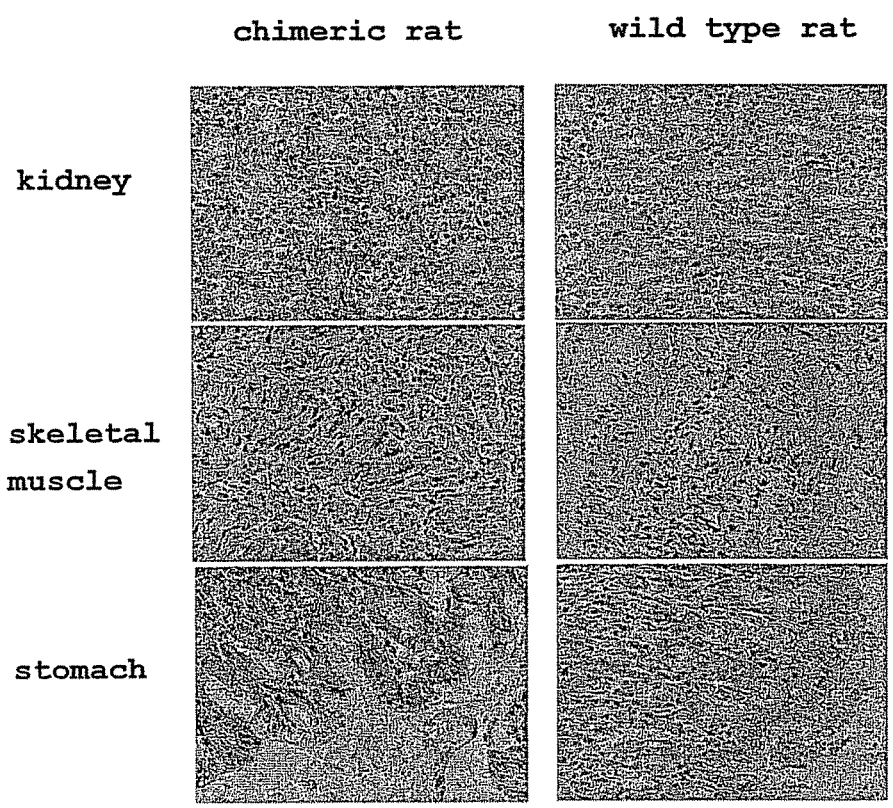
FIG. 25 shows photographs of each tissue (kidney, skeletal muscle and stomach) of a GFP chimeric rat sectioned and immunostained with anti-GFP antibody.

Using the GFP chimeric rat obtained in the aforementioned 5) and a syngeneic wild-type rat, each tissue was sectioned, and subjected to immunostaining using a GFP antibody (CLONTECH). The results are shown in FIG. 25. DAB-staining was confirmed only in the tissues of GFP chimeric rat, and it has been clarified that ES cell derived GFP-positive cell was certainly present in each tissue and expressed GFP.

The liver section of the GFP chimeric rat was fluorescence stained with Hoechst (blue) and rhodamin (red). As a result, a red region showing GFP-positive cells was confirmed near the central vein (data not shown).

From the above results, it has been clarified that not only a rat ES cell-derived gene is contained in each tissue but also the ES cell differentiated to the cell of each tissue lineage by morphological observation.

INDUSTRIAL APPLICABILITY

The present invention provides a rat ES cell. The established rat ES cell of the present invention has first enabled preparation of genetically modified rats (knockout rat, knockin rat etc.), and can be widely used for pharmacological studies and physiological studies in various regions such as cancer and cranial nerve, and further, studies on regenerative medicine and the like.

Sequence Listing Free Text

The base sequence described in SEQ ID NO:1 is a PCR primer.
The base sequence described in SEQ ID NO:2 is a PCR primer.
The base sequence described in SEQ ID NO:3 is a PCR primer.
The base sequence described in SEQ ID NO:4 is a PCR primer.
The base sequence described in SEQ ID NO:5 is a PCR primer.
The base sequence described in SEQ ID NO:6 is a PCR primer.
The base sequence described in SEQ ID NO:7 is a PCR primer.
The base sequence described in SEQ ID NO:8 is a PCR primer.
The base sequence described in SEQ ID NO:9 is a PCR primer.
The base sequence described in SEQ ID NO:10 is a PCR primer.
The base sequence described in SEQ ID NO:11 is a PCR primer.
The base sequence described in SEQ ID NO:12 is a PCR primer.
The base sequence described in SEQ ID NO:13 is a PCR primer.
The base sequence described in SEQ ID NO:14 is a PCR primer.
The base sequence described in SEQ ID NO:15 is a PCR primer.
The base sequence described in SEQ ID NO:16 is a PCR primer.
The base sequence described in SEQ ID NO:17 is a PCR primer.
The base sequence described in SEQ ID NO:18 is a PCR primer.
The base sequence described in SEQ ID NO:19 is a PCR primer.
The base sequence described in SEQ ID NO:20 is a PCR primer.
The base sequence described in SEQ ID NO:21 is a PCR primer.
The base sequence described in SEQ ID NO:22 is a PCR primer.
The base sequence described in SEQ ID NO:23 is a PCR primer.
The base sequence described in SEQ ID NO:24 is a PCR primer.
The base sequence described in SEQ ID NO:25 is a PCR primer.
The base sequence described in SEQ ID NO:26 is a PCR primer.
The base sequence described in SEQ ID NO:27 is a PCR primer.
The base sequence described in SEQ ID NO:28 is a PCR primer.
The base sequence described in SEQ ID NO:29 is a PCR primer.
The base sequence described in SEQ ID NO:30 is a PCR primer.
The base sequence described in SEQ ID NO:31 is a PCR primer.
The base sequence described in SEQ ID NO:32 is a PCR primer.

The invention claimed is:

1. A heterozygous knockout or knockin rat obtained by
(I) producing a chimeric rat by a process comprising the following steps (X)-(Z):
(X) a step for introducing a targeting vector into a target gene in the genome of a rat embryonic stem cell by homologous recombination to produce a homologously recombined rat embryonic stem cell,
(Y) a step for preparing a chimeric rat embryo for transplantation by (i) injecting the rat embryonic stem cell, into which the targeting vector was introduced, into a blastocoele of a rat blastocyst or a morula stage-, 16-cell stage- or 8-cell stage-rat embryo or (ii) co-culturing the rat embryonic stem cell, into which the targeting vector was introduced, with an 8-cell stage- or 16-cell stage-rat embryo without zona pellucidas,
(Z) a step for transferring the chimeric rat embryo for transplantation into the uterus of a pseudopregnant female rat to produce the chimeric rat, wherein the rat embryonic stem cell has the following properties (a)-(k):
(a) expressing Oct3/4 gene and Nanog gene,
(b) positive for alkaline phosphatase activity,
(c) having an embryoid body forming ability,
(d) expressing SSEA (Stage-Specific Embryonic Antigen)-1 and SSEA-4,
(e) having the same number of chromosomes as does a normal rat cell,
(f) capable of being subcultured and holding the undifferentiated state,
(g) having in vitro pluripotency,
(h) having a potential to differentiate for cells of three embryonic germ lineages,
(i) having teratoma formation ability,
(j) having an ability to produce a chimeric rat,
(k) being germline-competent,
wherein the rat embryonic stem cell is obtained by the method consisting essentially of the following steps (A)-(E) performed using a culture medium with 2% or less serum concentration:
(A) culturing a rat blastocyst on inactivated mouse embryonic fibroblasts in a leukemia inhibitory factor (LIF)-free culture medium to form an inner cell mass in the blastocyst,
(B) dissociating the inner cell mass, wherein the dissociated inner cell mass is in a cell aggregate state,
(C) culturing primary embryonic stem cells resulting from a culture of the dissociated inner cell mass on inactivated mouse embryonic fibroblasts until the primary embryonic stem cells can be passaged,
(D) dissociating the primary embryonic stem cells, which can be passaged, wherein the dissociated primary embryonic stem cells are in a cell aggregate state,
(E) culturing the dissociated primary embryonic stem cells on inactivated mouse embryonic fibroblasts to establish an embryonic stem cell,
wherein an rLIF-containing culture medium is used in steps (C)-(E); and
(II) crossing the chimeric rat with a wildtype rat, thereby producing a heterozygous knockout or knockin rat.

2. A homologous knockout or knockin rat obtained by mating the heterozygous knockout or knockin rats according to claim 1.

* * * * *